United States Patent
Kim et al.

(10) Patent No.: US 12,205,699 B1
(45) Date of Patent: Jan. 21, 2025

(54) METHOD OF PAIRING THERAPY DEVICES USING SHARED SECRETS, AND RELATED SYSTEMS, METHODS AND DEVICES

(71) Applicant: Bigfoot Biomedical, Inc., Milpitas, CA (US)

(72) Inventors: Aaron Kim, Milpitas, CA (US); Bryan Mazlish, Palo Alto, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 719 days.

(21) Appl. No.: 16/667,876

(22) Filed: Oct. 29, 2019

Related U.S. Application Data

(60) Provisional application No. 62/752,493, filed on Oct. 30, 2018.

(51) Int. Cl.
*H04L 9/32* (2006.01)
*A61B 5/00* (2006.01)
(Continued)

(52) U.S. Cl.
CPC ......... *G16H 20/17* (2018.01); *A61B 5/14532* (2013.01); *A61B 5/4839* (2013.01);
(Continued)

(58) Field of Classification Search
CPC ... H04L 9/3271; H04L 9/3236; H04L 9/3242; H04L 9/0869; H04L 2209/88;
(Continued)

(56) References Cited

U.S. PATENT DOCUMENTS

| | | |
|---|---|---|
| 4,498,904 A | 2/1985 | Turner et al. |
| 4,515,584 A | 5/1985 | Abe et al. |

(Continued)

FOREIGN PATENT DOCUMENTS

| | | |
|---|---|---|
| CA | 2925458 A1 | 4/2015 |
| CN | 201248860 Y | 6/2009 |

(Continued)

OTHER PUBLICATIONS

"Calculating Insulin Dose." Diabetes Education Online, University of California, San Francisco, https://web.archive.org/web/20110711172015/dtc.ucsf.edu/types-of-diabetes/type2/treatment-of-type-2-diabetes/medications-and-therapies/type-2-insulin-rx/calculating-insulin-dose/. Retrieved Feb. 2021. (Year: 2011).

(Continued)

*Primary Examiner* — Tae K Kim
(74) *Attorney, Agent, or Firm* — Sterne, Kessler, Goldstein & Fox P.L.L.C.

(57) ABSTRACT

Systems, methods and devices are described for establishing trusted connections among two or more therapy devices that form, or form part of, a medication therapy system. A medication delivery electronics may include a first communication interface, a connection manager, and a therapy management application. A first communication interface may be configured to establish and communicate over one or more communication links. A connection manager may be configured to generate a candidate shared secret key and provide the shared key to a first therapy device over a first communication link established by a first communication interface. A candidate shared key may be generated responsive to one or more shared secret parameters. A therapy management application may be configured to receive, using the first communication interface, the first therapy related information from the first therapy device over a first trusted communication link established by the first communication interface responsive to acceptance of a candidate shared secret.

14 Claims, 15 Drawing Sheets

(51) Int. Cl.
  *A61B 5/145* (2006.01)
  *A61M 5/142* (2006.01)
  *G16H 10/60* (2018.01)
  *G16H 20/17* (2018.01)
  *G16H 40/67* (2018.01)
  *H04L 9/08* (2006.01)

(52) U.S. Cl.
  CPC ........ *A61M 5/14244* (2013.01); *G16H 10/60* (2018.01); *G16H 40/67* (2018.01); *H04L 9/0866* (2013.01); *H04L 9/3236* (2013.01); *A61M 2230/201* (2013.01); *H04L 2209/12* (2013.01)

(58) Field of Classification Search
  CPC ... H04W 12/50; H04W 12/069; G06F 21/606; G06F 21/445; G06F 21/44; G16H 40/63; G16H 20/17
  See application file for complete search history.

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,233,571 A | 8/1993 | Wirtschafter |
| 5,279,586 A | 1/1994 | Balkwill |
| 5,523,560 A | 6/1996 | Manique et al. |
| 5,536,249 A | 7/1996 | Castellano et al. |
| 5,564,414 A | 10/1996 | Walker et al. |
| 5,626,566 A | 5/1997 | Petersen et al. |
| 5,640,954 A | 6/1997 | Pfeiffer et al. |
| 5,645,534 A | 7/1997 | Chanoch |
| 5,665,065 A | 9/1997 | Colman et al. |
| 5,678,571 A | 10/1997 | Brown |
| 5,681,285 A | 10/1997 | Ford et al. |
| 5,822,715 A | 10/1998 | Worthington et al. |
| 5,918,603 A | 7/1999 | Brown |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,032,119 A | 2/2000 | Brown et al. |
| 6,042,571 A | 3/2000 | Hjertman et al. |
| 6,235,004 B1 | 5/2001 | Steenfeldt-Jensen et al. |
| 6,287,283 B1 | 9/2001 | Ljunggreen et al. |
| 6,302,855 B1 | 10/2001 | Lav et al. |
| 6,354,996 B1 | 3/2002 | Drinan et al. |
| 6,482,185 B1 | 11/2002 | Hartmann |
| 6,650,951 B1 | 11/2003 | Jones et al. |
| 6,685,678 B2 | 2/2004 | Evans et al. |
| 6,810,290 B2 | 10/2004 | Lebel et al. |
| 6,817,986 B2 | 11/2004 | Slate et al. |
| 6,827,702 B2 | 12/2004 | Lebel et al. |
| 6,956,572 B2 | 10/2005 | Zaleski |
| 7,025,743 B2 | 4/2006 | Mann et al. |
| 7,109,878 B2 | 9/2006 | Mann et al. |
| 7,133,329 B2 | 11/2006 | Skyggebjerg et al. |
| 7,241,265 B2 | 7/2007 | Cummings et al. |
| 7,291,107 B2 | 11/2007 | Hellwig et al. |
| 7,343,197 B2 | 3/2008 | Shusterman |
| 7,397,730 B2 | 7/2008 | Skyggebjerg et al. |
| 7,404,796 B2 | 7/2008 | Ginsberg |
| 7,454,359 B2 | 11/2008 | Rosenfeld et al. |
| 7,553,281 B2 | 6/2009 | Hellwig et al. |
| 7,570,980 B2 | 8/2009 | Ginsberg |
| 7,591,801 B2 | 9/2009 | Brauker et al. |
| 7,647,237 B2 | 1/2010 | Malave et al. |
| 7,713,229 B2 | 5/2010 | Veit et al. |
| 7,751,907 B2 | 7/2010 | Blomquist |
| 7,837,647 B2 | 11/2010 | Estes et al. |
| 7,850,641 B2 | 12/2010 | Lebel et al. |
| 7,871,376 B2 | 1/2011 | Brown |
| 7,878,975 B2 | 2/2011 | Liljeryd et al. |
| 7,905,833 B2 | 3/2011 | Brister et al. |
| 7,931,613 B2 | 4/2011 | Haueter et al. |
| 7,955,303 B2 | 6/2011 | Burren et al. |
| 7,976,492 B2 | 7/2011 | Brauker et al. |
| 8,012,119 B2 | 9/2011 | Estes et al. |
| 8,052,655 B2 | 11/2011 | Moeller et al. |
| 8,108,299 B1 | 1/2012 | Waelbroeck et al. |
| 8,127,946 B2 | 3/2012 | Winig et al. |
| 8,132,101 B2 | 3/2012 | Buck et al. |
| 8,156,070 B2 | 4/2012 | Buck et al. |
| 8,206,340 B2 | 6/2012 | Arefieg |
| 8,217,946 B2 | 7/2012 | Halpern et al. |
| 8,219,222 B2 | 7/2012 | Blomquist |
| 8,221,345 B2 | 7/2012 | Blomquist |
| 8,221,356 B2 | 7/2012 | Enggaard et al. |
| 8,229,535 B2 | 7/2012 | Mensinger et al. |
| 8,231,531 B2 | 7/2012 | Brister et al. |
| 8,231,562 B2 | 7/2012 | Buck et al. |
| 8,237,715 B2 | 8/2012 | Buck et al. |
| 8,250,483 B2 | 8/2012 | Blomquist |
| D667,948 S | 9/2012 | Moldenhauer |
| 8,257,652 B2 | 9/2012 | Drucker et al. |
| 8,257,653 B2 | 9/2012 | Drucker et al. |
| 8,266,906 B2 | 9/2012 | Wu et al. |
| 8,273,296 B2 | 9/2012 | Drucker et al. |
| 8,279,226 B2 | 10/2012 | Krieftewirth |
| RE43,834 E | 11/2012 | Steenfeldt-Jensen et al. |
| 8,310,415 B2 | 11/2012 | McLaughlin et al. |
| 8,333,752 B2 | 12/2012 | Veit et al. |
| 8,337,469 B2 | 12/2012 | Eberhart et al. |
| 8,357,091 B2 | 1/2013 | Say et al. |
| 8,365,065 B2 | 1/2013 | Gejdos et al. |
| 8,372,005 B2 | 2/2013 | Say et al. |
| 8,439,834 B2 | 5/2013 | Schmelzeisen-Redeker et al. |
| 8,444,595 B2 | 5/2013 | Brukalo et al. |
| 8,460,231 B2 | 6/2013 | Brauker et al. |
| 8,514,086 B2 | 8/2013 | Harper et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| 8,551,039 B2 | 10/2013 | Veit et al. |
| 8,556,865 B2 | 10/2013 | Krulevitch et al. |
| 8,556,867 B2 | 10/2013 | Krulevitch et al. |
| 8,562,558 B2 | 10/2013 | Kamath et al. |
| 8,565,848 B2 | 10/2013 | Brister et al. |
| D694,252 S | 11/2013 | Helm |
| 8,579,815 B2 | 11/2013 | Galley et al. |
| 8,591,455 B2 | 11/2013 | Mensinger et al. |
| 8,601,005 B2 | 12/2013 | Bousamra et al. |
| 8,615,366 B2 | 12/2013 | Galley et al. |
| 8,622,906 B2 | 1/2014 | Say et al. |
| 8,657,779 B2 | 2/2014 | Blomquist |
| 8,663,109 B2 | 3/2014 | Brister et al. |
| 8,719,945 B2 | 5/2014 | Birtwhistle et al. |
| 8,721,585 B2 | 5/2014 | Brauker et al. |
| 8,738,925 B1 | 5/2014 | Park et al. |
| 8,743,662 B2 | 6/2014 | Sjolund et al. |
| 8,750,955 B2 | 6/2014 | Brister et al. |
| 8,756,074 B2 | 6/2014 | Brzustowicz |
| 8,761,940 B2 | 6/2014 | Long et al. |
| 8,774,887 B2 | 7/2014 | Say et al. |
| 8,808,228 B2 | 8/2014 | Brister et al. |
| 8,816,862 B2 | 8/2014 | Harper et al. |
| 8,817,258 B2 | 8/2014 | Whalley et al. |
| 8,821,452 B2 | 9/2014 | Dasbach et al. |
| 8,882,722 B2 | 11/2014 | Bode et al. |
| 8,882,741 B2 | 11/2014 | Brauker et al. |
| 8,895,315 B2 | 11/2014 | Batman et al. |
| 8,920,401 B2 | 12/2014 | Brauker et al. |
| 8,926,585 B2 | 1/2015 | Brauker et al. |
| 8,932,250 B2 | 1/2015 | Montgomery et al. |
| 8,961,465 B2 | 2/2015 | Blomquist |
| 8,992,464 B2 | 3/2015 | Bashan et al. |
| D727,928 S | 4/2015 | Allison et al. |
| 9,008,803 B2 | 4/2015 | Blomquist |
| 9,020,572 B2 | 4/2015 | Mensinger et al. |
| 9,022,996 B2 | 5/2015 | Eberhart et al. |
| 9,033,877 B2 | 5/2015 | Werner et al. |
| 9,041,730 B2 | 5/2015 | Johnson et al. |
| 9,050,409 B2 | 6/2015 | Haueter et al. |

(56) References Cited

U.S. PATENT DOCUMENTS

| | | |
|---|---|---|
| 9,050,413 B2 | 6/2015 | Brauker et al. |
| 9,072,477 B2 | 7/2015 | Say et al. |
| 9,089,650 B2 | 7/2015 | Nielsen et al. |
| 9,101,723 B2 | 8/2015 | Larsen |
| 9,108,006 B2 | 8/2015 | Jensen et al. |
| D738,385 S | 9/2015 | Lim et al. |
| 9,125,991 B2 | 9/2015 | Schabbach et al. |
| 9,134,823 B2 | 9/2015 | Grant et al. |
| 9,136,939 B2 | 9/2015 | Galley et al. |
| 9,143,569 B2 | 9/2015 | Mensinger et al. |
| 9,155,843 B2 | 10/2015 | Brauker et al. |
| 9,159,148 B2 | 10/2015 | Boyer et al. |
| 9,186,113 B2 | 11/2015 | Harper et al. |
| 9,198,623 B2 | 12/2015 | Fern et al. |
| D747,333 S | 1/2016 | Supino et al. |
| D748,101 S | 1/2016 | Bang et al. |
| D748,126 S | 1/2016 | Sarukkai et al. |
| 9,233,210 B2 | 1/2016 | Bock et al. |
| D749,103 S | 2/2016 | Song |
| 9,250,111 B2 | 2/2016 | Whalley et al. |
| 9,255,830 B2 | 2/2016 | Whalley et al. |
| D753,685 S | 4/2016 | Zimmerman et al. |
| D754,689 S | 4/2016 | Lee |
| D759,684 S | 6/2016 | Bijlani et al. |
| 9,358,334 B2 | 6/2016 | Arefieg |
| D761,280 S | 7/2016 | Chung et al. |
| D763,308 S | 8/2016 | Wang et al. |
| D766,958 S | 9/2016 | Salazar et al. |
| 9,435,666 B2 | 9/2016 | Richter |
| 9,446,194 B2 | 9/2016 | Kamath et al. |
| 9,483,620 B2 | 11/2016 | Reimer |
| 9,498,155 B2 | 11/2016 | Brauker et al. |
| 9,501,219 B2 | 11/2016 | Yoshimoto et al. |
| 9,526,838 B2 | 12/2016 | Baran et al. |
| D777,760 S | 1/2017 | Zhao et al. |
| 9,545,482 B2 | 1/2017 | Binier |
| 9,561,324 B2 | 2/2017 | Estes |
| D781,890 S | 3/2017 | Gathman et al. |
| 9,604,004 B2 | 3/2017 | Jakobsen |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| 9,619,625 B2 | 4/2017 | Bengtsson |
| 9,623,188 B2 | 4/2017 | Nielsen et al. |
| 9,629,901 B2 | 4/2017 | Estes |
| D786,273 S | 5/2017 | Herman et al. |
| 9,636,461 B2 | 5/2017 | Bengtsson et al. |
| 9,636,464 B1 | 5/2017 | Binier |
| 9,638,564 B2 | 5/2017 | Whalley et al. |
| 9,642,968 B2 | 5/2017 | Whalley et al. |
| 9,649,448 B2 | 5/2017 | Madsen |
| 9,651,482 B2 | 5/2017 | Blei et al. |
| 9,672,328 B2 | 6/2017 | Saint et al. |
| 9,675,761 B2 | 6/2017 | Hoeholt et al. |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| 9,721,176 B2 | 8/2017 | Prager |
| 9,730,621 B2 | 8/2017 | Cohen et al. |
| 9,734,302 B2 | 8/2017 | Nielsen et al. |
| 9,737,665 B2 | 8/2017 | Heumann et al. |
| D797,760 S | 9/2017 | Tsujimura et al. |
| D798,312 S | 9/2017 | Tsujimura et al. |
| 9,750,882 B2 | 9/2017 | Blei et al. |
| 9,750,886 B2 | 9/2017 | Plambech et al. |
| 9,775,543 B2 | 10/2017 | Brister et al. |
| 9,782,543 B2 | 10/2017 | Groeschke et al. |
| 9,782,544 B2 | 10/2017 | Heumann et al. |
| 9,788,172 B1 | 10/2017 | Ewe et al. |
| 9,789,260 B1 | 10/2017 | Binier |
| 9,790,977 B2 | 10/2017 | Baran et al. |
| D802,760 S | 11/2017 | Neby |
| 9,833,576 B2 | 12/2017 | Windum et al. |
| 9,848,774 B2 | 12/2017 | Bergstrom et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| D819,043 S | 5/2018 | Yamaura et al. |
| 9,980,140 B1 * | 5/2018 | Spencer ................ H04W 12/02 |
| D820,297 S | 6/2018 | Gardner et al. |
| 9,996,668 B2 | 6/2018 | Reihman et al. |
| 10,016,565 B2 | 7/2018 | Nielsen et al. |
| 10,043,093 B2 | 8/2018 | Allerdings et al. |
| 10,071,205 B2 | 9/2018 | Blei et al. |
| D831,049 S | 10/2018 | Agarwal et al. |
| D831,684 S | 10/2018 | Ghosh |
| D832,292 S | 10/2018 | Hu et al. |
| 10,086,141 B2 | 10/2018 | Steel et al. |
| 10,105,094 B2 | 10/2018 | Baran et al. |
| 10,105,497 B2 | 10/2018 | Dreier et al. |
| D832,870 S | 11/2018 | Hu |
| D833,469 S | 11/2018 | Coleman et al. |
| D834,710 S | 11/2018 | Michael |
| 10,117,996 B2 | 11/2018 | Stefansen |
| 10,117,999 B2 | 11/2018 | Andersen |
| 10,133,948 B2 | 11/2018 | Hammen |
| D835,118 S | 12/2018 | Lee et al. |
| 10,155,090 B2 | 12/2018 | Larsen et al. |
| 10,159,797 B2 | 12/2018 | Andersen et al. |
| 10,159,798 B2 | 12/2018 | Blei et al. |
| D837,807 S | 1/2019 | Baber et al. |
| D838,734 S | 1/2019 | Kruse et al. |
| 10,166,338 B2 | 1/2019 | Nielsen et al. |
| 10,166,340 B2 | 1/2019 | Blei et al. |
| 10,169,539 B2 | 1/2019 | Reihman et al. |
| 10,173,015 B2 | 1/2019 | Fiedler et al. |
| 10,179,207 B2 | 1/2019 | Haupt |
| 10,183,119 B2 | 1/2019 | Andersen et al. |
| 10,183,120 B2 | 1/2019 | Sihlanick et al. |
| 10,190,901 B2 | 1/2019 | Whalley et al. |
| 10,195,351 B2 | 2/2019 | Allerdings et al. |
| 10,195,352 B2 | 2/2019 | Baran et al. |
| 10,195,355 B2 | 2/2019 | Allerdings et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Kolbenheyer |
| D849,757 S | 5/2019 | Jing et al. |
| 10,296,128 B1 | 5/2019 | Nold et al. |
| 10,341,866 B1 * | 7/2019 | Spencer ................ G06F 21/602 |
| 10,524,110 B1 * | 12/2019 | Klem ..................... H04L 63/18 |
| 10,667,759 B2 | 6/2020 | Duke et al. |
| 10,686,898 B1 | 6/2020 | Phillips et al. |
| 10,702,658 B2 | 7/2020 | Shekalim |
| 10,896,245 B2 * | 1/2021 | Crothall ................ G16H 20/17 |
| 11,464,459 B2 | 10/2022 | Sjolund et al. |
| 2003/0028089 A1 | 2/2003 | Galley et al. |
| 2003/0032868 A1 | 2/2003 | Graskov et al. |
| 2003/0065536 A1 | 4/2003 | Hansen et al. |
| 2004/0039255 A1 | 2/2004 | Simonsen et al. |
| 2004/0062148 A1 | 4/2004 | Skyggebjerg et al. |
| 2004/0093331 A1 | 5/2004 | Garner et al. |
| 2004/0153257 A1 | 8/2004 | Munk |
| 2005/0005121 A1 * | 1/2005 | Chen ..................... H04L 9/3073 |
| | | 713/171 |
| 2005/0038674 A1 | 2/2005 | Braig et al. |
| 2005/0049179 A1 | 3/2005 | Davidson et al. |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0119705 A1 | 5/2008 | Patel et al. |
| 2008/0162192 A1 | 7/2008 | Vonk et al. |
| 2008/0188813 A1 | 8/2008 | Miller et al. |
| 2008/0201169 A1 | 8/2008 | Galasso et al. |

(56) References Cited

U.S. PATENT DOCUMENTS

| | | |
|---|---|---|
| 2008/0228057 A1 | 9/2008 | Graskov et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2008/0287755 A1 | 11/2008 | Sass et al. |
| 2008/0300572 A1 | 12/2008 | Rankers et al. |
| 2008/0310676 A1 | 12/2008 | Silver |
| 2008/0312512 A1 | 12/2008 | Brukalo et al. |
| 2008/0312584 A1 | 12/2008 | Montgomery et al. |
| 2009/0036771 A1 | 2/2009 | Fago et al. |
| 2009/0048561 A1 | 2/2009 | Burren et al. |
| 2009/0103124 A1 | 4/2009 | Kimura et al. |
| 2009/0120716 A1 | 5/2009 | Yamamoto et al. |
| 2009/0131875 A1 | 5/2009 | Green |
| 2009/0144089 A1 | 6/2009 | Heywood et al. |
| 2009/0163793 A1 | 6/2009 | Koehler et al. |
| 2009/0171589 A1 | 7/2009 | Kovatchev |
| 2009/0209938 A1 | 8/2009 | Matti |
| 2009/0240440 A1 | 9/2009 | Shurabura et al. |
| 2009/0299276 A1 | 12/2009 | Brauker et al. |
| 2009/0299279 A1 | 12/2009 | Richter |
| 2009/0318865 A1 | 12/2009 | Moeller et al. |
| 2010/0017141 A1 | 1/2010 | Campbell et al. |
| 2010/0049126 A1 | 2/2010 | Bronfeld et al. |
| 2010/0058060 A1* | 3/2010 | Schneider .............. H04L 9/3271 713/171 |
| 2010/0063438 A1 | 3/2010 | Bengtsson |
| 2010/0081993 A1 | 4/2010 | O'Connor |
| 2010/0095229 A1 | 4/2010 | Dixon et al. |
| 2010/0198520 A1 | 8/2010 | Breton et al. |
| 2010/0292634 A1 | 11/2010 | Kircher et al. |
| 2010/0305965 A1 | 12/2010 | Benjamin et al. |
| 2010/0331656 A1 | 12/2010 | Mensinger et al. |
| 2011/0009727 A1 | 1/2011 | Mensinger et al. |
| 2011/0124996 A1 | 5/2011 | Reinke et al. |
| 2011/0178462 A1 | 7/2011 | Moberg et al. |
| 2011/0184343 A1 | 7/2011 | Veit et al. |
| 2011/0191343 A1 | 8/2011 | Heaton et al. |
| 2011/0193704 A1 | 8/2011 | Harper et al. |
| 2011/0201911 A1 | 8/2011 | Johnson et al. |
| 2011/0270158 A1 | 11/2011 | Brauker et al. |
| 2011/0275986 A1 | 11/2011 | Bashan et al. |
| 2011/0281791 A1 | 11/2011 | Zion et al. |
| 2011/0282409 A1 | 11/2011 | Ternes et al. |
| 2011/0295215 A1 | 12/2011 | Nielsen et al. |
| 2011/0313350 A1 | 12/2011 | Krulevitch et al. |
| 2011/0313395 A1 | 12/2011 | Krulevitch et al. |
| 2012/0046606 A1 | 2/2012 | Arefieg |
| 2012/0072236 A1 | 3/2012 | Atkin |
| 2012/0078665 A1 | 3/2012 | Johnson et al. |
| 2012/0165746 A1 | 6/2012 | Harms et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0238853 A1 | 9/2012 | Arefieg |
| 2012/0271557 A1 | 10/2012 | Sekimoto et al. |
| 2012/0296311 A1 | 11/2012 | Brauker et al. |
| 2013/0004844 A1 | 1/2013 | Hosoe et al. |
| 2013/0030841 A1 | 1/2013 | Bergstrom et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0047084 A1 | 2/2013 | Sanders et al. |
| 2013/0171938 A1 | 7/2013 | Mears et al. |
| 2013/0184547 A1 | 7/2013 | Taub et al. |
| 2013/0184996 A1 | 7/2013 | Zivitz et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2013/0298063 A1 | 11/2013 | Joy et al. |
| 2013/0310756 A1 | 11/2013 | Whalley et al. |
| 2013/0331659 A1 | 12/2013 | Koski et al. |
| 2013/0338453 A1 | 12/2013 | Duke et al. |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0018733 A1 | 1/2014 | Sjoelund et al. |
| 2014/0019396 A1 | 1/2014 | Carlsgaard et al. |
| 2014/0025400 A1 | 1/2014 | Galley et al. |
| 2014/0058749 A1 | 2/2014 | Galley et al. |
| 2014/0068487 A1 | 3/2014 | Steiger et al. |
| 2014/0074041 A1 | 3/2014 | Pedersen et al. |
| 2014/0081662 A1 | 3/2014 | Bradrick et al. |
| 2014/0091941 A1 | 4/2014 | Johnson et al. |
| 2014/0094743 A1 | 4/2014 | Bengtsson |
| 2014/0113856 A1 | 4/2014 | Pohl et al. |
| 2014/0114161 A1 | 4/2014 | Kamath et al. |
| 2014/0128705 A1 | 5/2014 | Mazlish |
| 2014/0148659 A1 | 5/2014 | Sloan et al. |
| 2014/0187889 A1 | 7/2014 | Cohen et al. |
| 2014/0200426 A1 | 7/2014 | Taub et al. |
| 2014/0207080 A1 | 7/2014 | Allerdings |
| 2014/0257065 A1 | 9/2014 | Brister et al. |
| 2014/0276531 A1 | 9/2014 | Walsh |
| 2014/0288494 A1 | 9/2014 | Brister et al. |
| 2014/0297299 A1 | 10/2014 | Lester, IV |
| 2014/0309615 A1 | 10/2014 | Mazlish |
| 2014/0324020 A1 | 10/2014 | Stefansen |
| 2014/0371682 A1 | 12/2014 | Bengtsson et al. |
| 2015/0018770 A1 | 1/2015 | Baran et al. |
| 2015/0043410 A1 | 2/2015 | Chaturvedi et al. |
| 2015/0073337 A1 | 3/2015 | Saint et al. |
| 2015/0151050 A1 | 6/2015 | Estes |
| 2015/0164415 A1 | 6/2015 | Bashan et al. |
| 2015/0193595 A1 | 7/2015 | McNamara et al. |
| 2015/0202375 A1 | 7/2015 | Schabbach et al. |
| 2015/0202377 A1 | 7/2015 | Haupt |
| 2015/0205947 A1 | 7/2015 | Berman et al. |
| 2015/0246179 A1 | 9/2015 | Zur et al. |
| 2015/0260726 A1 | 9/2015 | Refvik |
| 2015/0289823 A1 | 10/2015 | Rack-Gomer et al. |
| 2015/0290396 A1 | 10/2015 | Nagar et al. |
| 2015/0306304 A1 | 10/2015 | Schabbach et al. |
| 2015/0350147 A1 | 12/2015 | Shepherd et al. |
| 2015/0351683 A1 | 12/2015 | Brauker et al. |
| 2015/0356273 A1 | 12/2015 | Cave |
| 2015/0359490 A1 | 12/2015 | Massey et al. |
| 2015/0359965 A1 | 12/2015 | O'Connor et al. |
| 2015/0365826 A1* | 12/2015 | Mancini ................ G16H 40/63 713/155 |
| 2016/0030673 A1 | 2/2016 | White et al. |
| 2016/0030679 A1 | 2/2016 | Nielsen et al. |
| 2016/0030680 A1 | 2/2016 | Veasey et al. |
| 2016/0030683 A1 | 2/2016 | Taylor et al. |
| 2016/0038675 A1 | 2/2016 | Estes et al. |
| 2016/0047685 A1 | 2/2016 | Blei et al. |
| 2016/0047743 A1 | 2/2016 | Blei et al. |
| 2016/0051760 A1 | 2/2016 | Krusell et al. |
| 2016/0065799 A1 | 3/2016 | Haupt et al. |
| 2016/0066843 A1 | 3/2016 | Mensinger et al. |
| 2016/0081632 A1 | 3/2016 | Kamath et al. |
| 2016/0082192 A1 | 3/2016 | Veasey et al. |
| 2016/0101232 A1 | 4/2016 | Kamath et al. |
| 2016/0101234 A1 | 4/2016 | Bock et al. |
| 2016/0106927 A1 | 4/2016 | Moeller et al. |
| 2016/0113558 A1 | 4/2016 | Bhavaraju et al. |
| 2016/0117481 A1 | 4/2016 | Booth et al. |
| 2016/0155081 A1 | 6/2016 | Legisa et al. |
| 2016/0213848 A1 | 7/2016 | Whalley et al. |
| 2016/0223380 A1 | 8/2016 | Whalley et al. |
| 2016/0235925 A1 | 8/2016 | Kuhn et al. |
| 2016/0263327 A1 | 9/2016 | Radmer et al. |
| 2016/0266752 A1 | 9/2016 | Wu et al. |
| 2016/0287804 A1 | 10/2016 | Madsen et al. |
| 2016/0287807 A1 | 10/2016 | Madsen et al. |
| 2016/0324463 A1 | 11/2016 | Simpson et al. |
| 2017/0053101 A1 | 2/2017 | Booth et al. |
| 2017/0053552 A1 | 2/2017 | Zhong et al. |
| 2017/0068799 A1 | 3/2017 | Mensinger et al. |
| 2017/0103175 A1 | 4/2017 | Chopra et al. |

(56) References Cited

U.S. PATENT DOCUMENTS

| | | |
|---|---|---|
| 2017/0106052 A1 | 4/2017 | Spat et al. |
| 2017/0124275 A1 | 5/2017 | Reihman et al. |
| 2017/0131993 A1 | 5/2017 | Salameh et al. |
| 2017/0132120 A1 | 5/2017 | Salameh et al. |
| 2017/0132392 A1 | 5/2017 | Gerken |
| 2017/0138769 A1 | 5/2017 | Jones et al. |
| 2017/0139974 A1 | 5/2017 | Javed et al. |
| 2017/0151390 A1 | 6/2017 | Muller-Pathle |
| 2017/0173261 A1 | 6/2017 | O'Connor et al. |
| 2017/0181645 A1 | 6/2017 | Mahalingam et al. |
| 2017/0181678 A1 | 6/2017 | Newberry |
| 2017/0182258 A1 | 6/2017 | Michael |
| 2017/0185283 A1 | 6/2017 | Bhavaraju et al. |
| 2017/0185284 A1 | 6/2017 | Bhavaraju et al. |
| 2017/0189615 A1 | 7/2017 | Estes |
| 2017/0189616 A1 | 7/2017 | Bengtsson et al. |
| 2017/0189625 A1 | 7/2017 | Cirillo et al. |
| 2017/0199985 A1 | 7/2017 | Mazlish et al. |
| 2017/0215811 A1 | 8/2017 | Newberry |
| 2017/0216518 A1 | 8/2017 | Davis et al. |
| 2017/0216524 A1 | 8/2017 | Haider et al. |
| 2017/0219486 A1 | 8/2017 | Blei et al. |
| 2017/0220751 A1 | 8/2017 | Davis et al. |
| 2017/0224922 A1 | 8/2017 | Lepple-Wienhues |
| 2017/0224927 A1 | 8/2017 | Windum et al. |
| 2017/0228518 A1 | 8/2017 | Booth et al. |
| 2017/0232203 A1 | 8/2017 | Krusell |
| 2017/0235919 A1 | 8/2017 | Bauss et al. |
| 2017/0235920 A1 | 8/2017 | Bauss et al. |
| 2017/0251982 A1 | 9/2017 | Koehler et al. |
| 2017/0266389 A1 | 9/2017 | McLoughlin et al. |
| 2017/0270276 A1 | 9/2017 | Saint et al. |
| 2017/0270829 A1 | 9/2017 | Bauss |
| 2017/0286194 A1 | 10/2017 | Morris et al. |
| 2017/0286614 A1 | 10/2017 | Morris et al. |
| 2017/0286638 A1 | 10/2017 | Searle et al. |
| 2017/0304538 A1 | 10/2017 | Renstad et al. |
| 2017/0304541 A1 | 10/2017 | Bauss et al. |
| 2017/0304552 A1 | 10/2017 | Prager |
| 2017/0312446 A1 | 11/2017 | Kunz et al. |
| 2017/0316178 A1 | 11/2017 | Riedel et al. |
| 2017/0338864 A1 | 11/2017 | Rolsted et al. |
| 2017/0340808 A1 | 11/2017 | Andersen et al. |
| 2017/0340826 A1 | 11/2017 | Draper |
| 2017/0351842 A1 | 12/2017 | Booth et al. |
| 2017/0366617 A1 | 12/2017 | Mensinger et al. |
| 2017/0367627 A1 | 12/2017 | Brister et al. |
| 2017/0368263 A1 | 12/2017 | Ploch |
| 2017/0368265 A1 | 12/2017 | Groeschke et al. |
| 2018/0001027 A1 | 1/2018 | Klemm et al. |
| 2018/0008773 A1 | 1/2018 | Hautaviita et al. |
| 2018/0008778 A1 | 1/2018 | Erbstein |
| 2018/0008779 A1 | 1/2018 | Hautaviita et al. |
| 2018/0028759 A1 | 2/2018 | Riedel et al. |
| 2018/0028760 A1 | 2/2018 | Gugl et al. |
| 2018/0036484 A1 | 2/2018 | Andersen |
| 2018/0036495 A1 | 2/2018 | Searle et al. |
| 2018/0042559 A1 | 2/2018 | Cabrera et al. |
| 2018/0043104 A1 | 2/2018 | Mueller Pathle |
| 2018/0050157 A1 | 2/2018 | Whalley et al. |
| 2018/0060008 A1 | 3/2018 | Bender et al. |
| 2018/0060529 A1* | 3/2018 | Crothall ................. G16H 40/67 |
| 2018/0064879 A1 | 3/2018 | Sall et al. |
| 2018/0085532 A1 | 3/2018 | Desborough et al. |
| 2018/0099084 A1 | 4/2018 | Schabbach et al. |
| 2018/0103879 A1 | 4/2018 | Masciotti et al. |
| 2018/0121630 A1 | 5/2018 | Portnoy |
| 2018/0147362 A1 | 5/2018 | Arenas et al. |
| 2018/0154086 A1 | 6/2018 | Toporek et al. |
| 2018/0161505 A1 | 6/2018 | Prager |
| 2018/0185587 A1 | 7/2018 | Brauker et al. |
| 2018/0217917 A1 | 8/2018 | Hayter et al. |
| 2018/0221582 A1 | 8/2018 | Klemm et al. |
| 2018/0224315 A1 | 8/2018 | Schabbacha et al. |
| 2018/0226150 A1 | 8/2018 | Hayter et al. |
| 2018/0228977 A1 | 8/2018 | Schabbach et al. |
| 2018/0236172 A1 | 8/2018 | Schabbach et al. |
| 2018/0236185 A1 | 8/2018 | Sall et al. |
| 2018/0243504 A1 | 8/2018 | Scott et al. |
| 2018/0262578 A1 | 9/2018 | Shaw et al. |
| 2018/0268236 A1 | 9/2018 | Klemm |
| 2018/0272072 A1 | 9/2018 | Radmer et al. |
| 2018/0277246 A1 | 9/2018 | Zhong et al. |
| 2018/0289901 A1 | 10/2018 | Bggild-Damkvist et al. |
| 2018/0296767 A1 | 10/2018 | Sall |
| 2018/0303417 A1 | 10/2018 | Mensinger et al. |
| 2018/0304028 A1 | 10/2018 | Riedel |
| 2018/0326164 A1 | 11/2018 | Bauss et al. |
| 2018/0339113 A1 | 11/2018 | Wendland et al. |
| 2018/0341826 A1 | 11/2018 | Allerdings et al. |
| 2018/0353694 A1 | 12/2018 | Riedel et al. |
| 2018/0353698 A1 | 12/2018 | Saint et al. |
| 2018/0353699 A1 | 12/2018 | Helmer et al. |
| 2018/0353700 A1 | 12/2018 | Sall et al. |
| 2018/0361067 A1 | 12/2018 | Sall et al. |
| 2018/0361076 A1 | 12/2018 | Klemm et al. |
| 2018/0361082 A1 | 12/2018 | Sall et al. |
| 2018/0368683 A1 | 12/2018 | Hu et al. |
| 2018/0369479 A1 | 12/2018 | Hayter et al. |
| 2018/0369488 A1 | 12/2018 | Carlsson et al. |
| 2018/0369490 A1 | 12/2018 | Rehbein et al. |
| 2019/0001060 A1 | 1/2019 | Gylleby et al. |
| 2019/0001069 A1 | 1/2019 | Carlsson et al. |
| 2019/0009032 A1 | 1/2019 | Hautaviita et al. |
| 2019/0015020 A1 | 1/2019 | Brister et al. |
| 2019/0015596 A1 | 1/2019 | Saint et al. |
| 2019/0022320 A1 | 1/2019 | Carlsson et al. |
| 2019/0029590 A1 | 1/2019 | Baran et al. |
| 2019/0030250 A1 | 1/2019 | Steel et al. |
| 2019/0035500 A1 | 1/2019 | Saint et al. |
| 2019/0036688 A1* | 1/2019 | Wasily ................. H04L 9/3231 |
| 2019/0076070 A1 | 3/2019 | Nogueira et al. |
| 2019/0125224 A1 | 5/2019 | Kamath et al. |
| 2019/0125969 A1 | 5/2019 | Montgomery et al. |
| 2019/0132801 A1 | 5/2019 | Kamath et al. |
| 2019/0149887 A1 | 5/2019 | Williams et al. |
| 2019/0173885 A1 | 6/2019 | Kamath et al. |
| 2019/0175833 A1 | 6/2019 | Sjolund et al. |
| 2019/0175841 A1 | 6/2019 | Sjolund et al. |
| 2019/0183434 A1 | 6/2019 | Sjolund et al. |
| 2019/0184091 A1 | 6/2019 | Sjolund et al. |
| 2019/0184092 A1 | 6/2019 | Sjolund et al. |
| 2019/0184093 A1 | 6/2019 | Sjolund et al. |
| 2019/0184094 A1 | 6/2019 | Sjolund et al. |
| 2019/0184107 A1 | 6/2019 | Sjolund et al. |
| 2019/0184108 A1 | 6/2019 | Sjolund et al. |
| 2019/0184109 A1 | 6/2019 | Sjolund et al. |
| 2019/0184111 A1 | 6/2019 | Sjolund et al. |
| 2019/0192071 A1 | 6/2019 | Taub et al. |
| 2019/0237181 A1 | 8/2019 | Steinberg |
| 2019/0239825 A1 | 8/2019 | Kumar et al. |
| 2019/0274598 A1 | 9/2019 | Scott et al. |
| 2019/0282141 A1 | 9/2019 | Causey et al. |
| 2019/0332774 A1* | 10/2019 | Nix ..................... H04W 12/50 |
| 2020/0016336 A1 | 1/2020 | Patek et al. |
| 2020/0205724 A1 | 7/2020 | Lee et al. |
| 2020/0261673 A1* | 8/2020 | Hickey ................. H04L 9/085 |
| 2020/0350052 A1 | 11/2020 | Saint et al. |
| 2020/0360794 A1 | 11/2020 | Intonato et al. |

FOREIGN PATENT DOCUMENTS

| | | |
|---|---|---|
| CN | 103443798 A | 12/2013 |
| CN | 103957961 A | 7/2014 |
| CN | 104411349 A | 3/2015 |
| CN | 104797282 A | 7/2015 |
| CN | 105377118 A | 3/2016 |
| CN | 107073207 A | 8/2017 |
| EP | 0298067 A1 | 1/1989 |
| EP | 0513128 A1 | 11/1992 |
| EP | 0927057 A1 | 7/1999 |
| EP | 1571582 A2 | 9/2005 |
| EP | 1680175 | 7/2006 |
| EP | 2401011 | 1/2012 |

(56) References Cited

FOREIGN PATENT DOCUMENTS

| | | |
|---|---|---|
| EP | 2572740 A1 | 3/2013 |
| EP | 2767297 A2 | 8/2014 |
| EP | 2911717 | 9/2015 |
| EP | 2926846 A1 | 10/2015 |
| EP | 3049132 A1 | 8/2016 |
| EP | 2879740 B1 | 3/2017 |
| EP | 3167393 A2 | 5/2017 |
| EP | 2797660 B1 | 10/2019 |
| JP | 2014-514046 A | 6/2014 |
| JP | 2014-531283 A | 11/2014 |
| JP | 2015-178044 A | 10/2015 |
| JP | 2016-515452 A | 5/2016 |
| JP | 2016-517601 A | 6/2016 |
| JP | 6058673 B2 | 1/2017 |
| WO | 85/02544 A1 | 6/1985 |
| WO | 91/10460 A1 | 7/1991 |
| WO | 96/38190 A1 | 12/1996 |
| WO | 98/10813 A1 | 3/1998 |
| WO | 2005/046559 A2 | 5/2005 |
| WO | 2010/037828 A1 | 4/2010 |
| WO | 2010/052275 A2 | 5/2010 |
| WO | 2010/056718 A2 | 5/2010 |
| WO | 2010/098927 A1 | 9/2010 |
| WO | 2011/041007 A1 | 4/2011 |
| WO | 2011/091238 A1 | 7/2011 |
| WO | 2012/046199 A1 | 4/2012 |
| WO | 2013/004844 A1 | 1/2013 |
| WO | 2013/037754 A2 | 3/2013 |
| WO | 2013/053695 A1 | 4/2013 |
| WO | 2013/177135 A1 | 11/2013 |
| WO | 2014/020010 A2 | 2/2014 |
| WO | 2014/029621 A1 | 2/2014 |
| WO | 2014/064691 A2 | 5/2014 |
| WO | 2014/128157 A1 | 8/2014 |
| WO | 2014/145049 A2 | 9/2014 |
| WO | 2015/047870 A1 | 4/2015 |
| WO | 2015/169814 A1 | 11/2015 |
| WO | 2015/185686 A1 | 12/2015 |
| WO | 2016/004210 A1 | 1/2016 |
| WO | 2016/019192 A1 | 2/2016 |
| WO | 2016/007935 A3 | 4/2016 |
| WO | 2016/071912 A1 | 5/2016 |
| WO | WO-2016116853 A1 * | 7/2016 ......... G06F 19/3418 |
| WO | 2016/151973 A1 | 9/2016 |
| WO | 2017/123523 A1 | 7/2017 |
| WO | 2017/123525 A1 | 7/2017 |
| WO | 2017/132557 A1 | 8/2017 |
| WO | 2017/132577 A1 | 8/2017 |
| WO | 2018/064222 A1 | 4/2018 |

OTHER PUBLICATIONS

Baker, New Technologies for Diabetes, Mar. 25, 2017, XP055568829, 76, https://diabetes-education.com/wp-content/uploads/2017/03/Baker-HCP3.pdf.

Hu et al., An Improved PID Algorithm Based on Insulin-on-Board Estimate for Blood Glucose Control with Type 1 Diabetes, Jan. 1, 2015, Computational and Mathematical Methods in Medicine, 1-8, 2015.

Near Field Communication versus Bluetooth, Jan. 3, 2016, NearFieldCommunication.org via web.archive.org (Year: 2016).

Sara Krugman, Bionic Pancreas User Interface (3/4): Interface Details, Tidepool.org, Jul. 20, 2015.

T:slimx2 Insulin Pump User Guide, Tandem Diabetes Care, Jul. 22, 2016.

White, Common Sensing, May 2, 2017, XP055568837, 15, Mar. 13, 2019.

Cision PR News Wire, "Companion Medical Announces Insights by InPen, the Future of MDI Reports", Jun. 20, 2018.

Chinese First Office Action and Search Report for Chinese Application No. 201880080537.X, dated Apr. 27, 2023, 53 pages with translation.

Chinese First Office Action and Search Report for Chinese Application No. 201880080699.3, dated May 11, 2023, 47 pages with translation.

European Communication pursuant to Article 94(3) EPC for European Application No. 18839959, dated Apr. 4, 2023, 6 pages.

European Communication pursuant to Article 94(3) EPC for European Application No. 18839960.4, dated May 26, 2023, 6 pages.

European Examination Report for EP Application No. 18840106.1, mailed Mar. 24, 2023, 14 pages.

European Search Report and Search Opinion Received for EP Application No. 21212980.3, dated on Jul. 7, 2022, 10 pages.

Hu et al., An Improved PID Algorithm Based on Insulin-on-Board Estimate for Blood Glucose Control with Type 1 Diabetes, Jan. 1, 2015, Computational and Mathematical Methods in Medicine, pp. 1-8, 2015.

Indian Patent Examination Report for Indian Application No. 202027023258 dated May 19, 2022, 6 pages.

Japanese Notice of Reasons for Refusal for Japanese Patent Application No. 2020-551774, dated Dec. 4, 2023, 14 pages with English translation.

Australian Patent Examination Report No. 1 for Australian Patent Application No. 2018383731, dated Oct. 17, 2023, 6 pages.

Australian Patent Examination Report No. 1 for Australian Patent Application No. 2018383743, dated Oct. 23, 2023, 5 pages.

Chinese Second Office Action for Chinese Application No. 201880080537.X, dated Nov. 10, 2023, 44 pages with English translation.

Chinese Second Office Action for Chinese Application No. 201880080699.3, dated Dec. 25, 2023, 33 pages with English translation.

Communication pursuant to Article 94(3) EPC for European Patent Application No. 18 852 783.2, mailed Jun. 22, 2023, 9 pages.

Japanese Notice of Reasons for Rejection for Japanese Application No. 2020-551774, dated Sep. 25, 2023, 6 pages with English translation.

Summons to attend oral proceedings pursuant to Rule 115(1) EPC for European Application No. 18839960.4, dated Jan. 25, 2024, 7 pages.

* cited by examiner

170

Receive a request for shared secret parameters from a first therapy device trying to establish a trusted communication link with a second therapy device
171

Reply to the request for shared secret parameters responsive to one or more therapy system policies and/or a search of therapy system records, wherein the therapy system policies describe restrictions that apply to therapy devices and the therapy system records describe one or more groups of therapy devices
172

```
┌─────────────────────────────────────────────────────────────────┐
│  Establish intermediate communication link with a therapy device │
│                              191                                 │
└─────────────────────────────────────────────────────────────────┘
                                 ↓
┌─────────────────────────────────────────────────────────────────┐
│  Send shared secret request to the therapy device over the       │
│                   intermediate communication link                │
│                              192                                 │
└─────────────────────────────────────────────────────────────────┘
                                 ↓
┌─────────────────────────────────────────────────────────────────┐
│  Receive a candidate shared secret key from the therapy device   │
│              over the intermediate communication link            │
│                              193                                 │
└─────────────────────────────────────────────────────────────────┘
                                 ↓
┌─────────────────────────────────────────────────────────────────┐
│ Validate a candidate shared secret responsive to a primary shared│
│ secret, wherein the primary shared secret is either stored or    │
│                      calculated locally                          │
│                              194                                 │
└─────────────────────────────────────────────────────────────────┘
                                 ↓
┌─────────────────────────────────────────────────────────────────┐
│   Establishing a trusted communication link with the therapy     │
│   device responsive to the comparison, wherein the trusted       │
│   communication link enables transmission of first therapy       │
│       related information to the first therapy device            │
│                              195                                 │
└─────────────────────────────────────────────────────────────────┘
```

```
┌─────────────────────────────────────────────────────────────────────┐
│  Generate a candidate shared secret key responsive to one or more  │
│  locally stored shared secret parameters and locally stored shared │
│  secret operations                                                  │
│                              332                                    │
└─────────────────────────────────────────────────────────────────────┘
                                  │
                                  ▼
┌─────────────────────────────────────────────────────────────────────┐
│  Provide the candidate shared secret key to a therapy related      │
│  device over an intermediate communication link                    │
│                              334                                    │
└─────────────────────────────────────────────────────────────────────┘
                                  │
                                  ▼
┌─────────────────────────────────────────────────────────────────────┐
│  Establish a trusted communication link with a therapy related     │
│  device responsive to an acceptance of a candidate shared secret,  │
│  wherein the trusted communication link enables receipt of first   │
│  therapy related information from the first therapy device         │
│                              336                                    │
└─────────────────────────────────────────────────────────────────────┘
```

*FIGURE 10*

METHOD OF PAIRING THERAPY DEVICES USING SHARED SECRETS, AND RELATED SYSTEMS, METHODS AND DEVICES

CROSS-REFERENCE TO RELATED APPLICATION

This application claims the benefit under 35 U.S.C. § 119(e) of U.S. Provisional Patent Application Ser. No. 62/752,493, filed Oct. 30, 2018, the disclosure of which is hereby incorporated herein in its entirety by this reference.

TECHNICAL FIELD

Embodiments of this disclosure relate, generally, to medication therapy systems, and more specifically, some embodiments relate to systems and methods for establishing trusted connections among two or more therapy devices that form a medication therapy system.

BACKGROUND

Medication delivery devices are commonly used to deliver medication to the human body, including as part of a medical treatment provided as a therapy for a medical condition. Medication delivery devices such as a transdermal liquid dosing device (e.g., an injection pen), inhalers, and syringes provide a convenient, often reusable means of delivering medication to the human body in fluid or aerosolized form. Infusion pumps also provide a convenient means of delivering medication to the human body in controlled amounts of fluid, and are often used when there is a desire to deliver medication in precisely calculated volumes (large and small) at precise rates and/or intervals. By way of example, medication delivery means may deliver medication intravenously, subcutaneously, arterially, and epidurally (i.e., via the epidural space around the spinal cord). Infusion pumps use a variety of techniques to deliver medication that do not require any or only a limited amount of manual manipulation. By way of example, infusion pumps may use positive displacement (e.g., a peristaltic pump, diaphragm pump, etc.), positive pressure (e.g., a drive system that advances a plunger), reciprocating positive pressure (e.g., plunger pumps that draw medication from a cartridge into a delivery chamber), and more.

One advantage of infusion pumps is that their dimensions may be such that they can be worn "on the body." For example, on-body infusion pumps are sometimes used for subcutaneous delivery of medication—the infusion pump delivers medication via a subcutaneous cannula, and an adhesive patch secures the pump, cannula and any other elements of the infusion set at the infusion site. The adhesive helps maintain the cannula in fluidic communication with the tissue and/or vasculature of the patient so that medication may be delivered to the patient's body.

Medication delivery devices are sometimes used in combination with other therapy related devices to deliver therapeutic amounts of medication. For example, when a treatment is based, at least in part, on an amount of an analyte in a patient's blood stream. An analyte sensor may be used to detect and/or measure amounts of the analyte and provide analyte data to a user, a medication delivery device, or other therapy related devices. A therapy application may store and analyze the analyte data, plan therapy activities, provide and receive information from users (e.g., via an interface), provide recommendations to users (e.g., via an interface), and, in some arrangements, provide instructions to a medication delivery device for medication delivery.

Medication therapies can exact a toll on users that, due to dangers associated with administering external biologically effective medication (e.g., hormone, analgesics, antibiotics, nutrients, etc.), must track, plan, and calculate amounts of medication delivered. So, therapy applications can be a tremendous boon, and off-load some of the cognitive and emotional burden associated with a medication therapy.

BRIEF DESCRIPTION OF DRAWINGS

While this disclosure concludes with claims particularly pointing out and distinctly claiming specific embodiments, various features and advantages of embodiments within the scope of this disclosure may be more readily ascertained from the following description when read in conjunction with the accompanying drawings, in which:

FIG. 6 is a flowchart of a process for enforcing policies for establishing trusted communication links among therapy devices, in accordance with one or more embodiments of the disclosure.

FIG. 8 is a flowchart of a process for establishing trusted communication links with a therapy device, in accordance with one or more embodiments of the disclosure.

FIG. 10 shows a flowchart of a process for establishing a trusted communication link with another therapy related device, in accordance with one or more embodiments of the disclosure.

DETAILED DESCRIPTION

Figure 1:
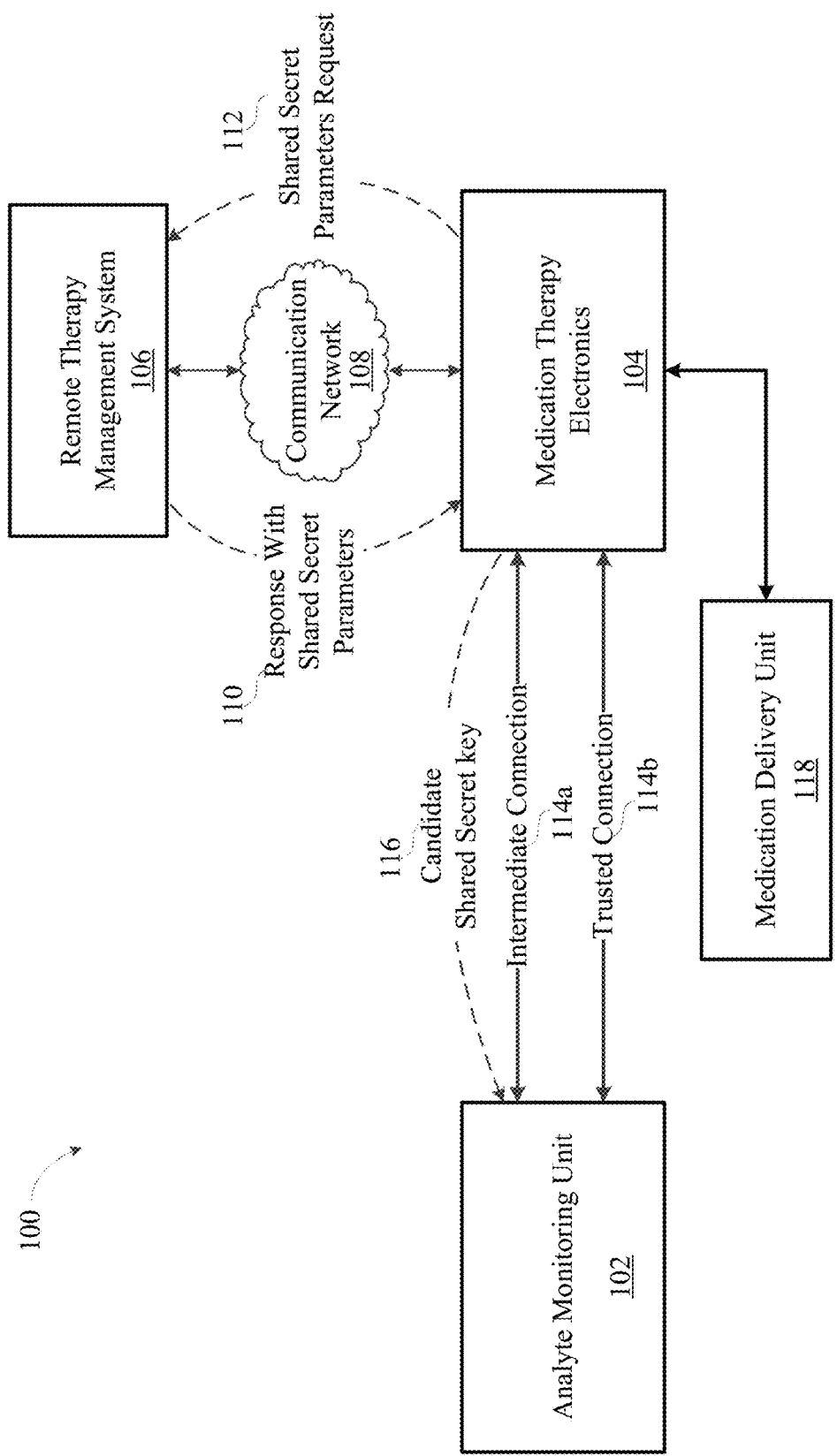
FIG. 1 is a functional block diagram of a therapy system, which includes at least some therapy devices that are configured to establish trusted connections in accordance with one or more embodiments of the disclosure.

In the following detailed description, reference is made to the accompanying drawings, which form a part hereof, and in which are shown, by way of illustration, specific example embodiments in which the present disclosure may be practiced. These embodiments are described in sufficient detail to enable a person of ordinary skill in the art to practice the present disclosure. However, other embodiments may be utilized, and structural, material, and process changes may be made without departing from the scope of the disclosure.

It should be understood that any reference to an element herein using a designation such as "first," "second," and so forth does not limit the quantity or order of those elements, unless such limitation is explicitly stated. Rather, these designations are used herein as a convenient method of distinguishing between two or more elements or instances of an element. Thus, a reference to first and second elements does not mean that only two elements can be employed or that the first element must precede the second element in some manner. Also, unless stated otherwise a set of elements may comprise one or more elements. Likewise, sometimes elements referred to in the singular form may also include one or more instances of the element.

The following description may include examples to help enable one of ordinary skill in the art to practice the disclosed embodiments. The use of the terms "exemplary," "by example," and "for example," means that the related description is explanatory, and though the scope of the disclosure is intended to encompass the examples and legal equivalents, the use of such terms is not intended to limit the scope of an embodiment or this disclosure to the specified components, steps, features, functions, or the like.

Sometimes therapy devices are wirelessly connected to each other to form a therapy system that is configured for medication delivery. For example, an analyte monitoring device may be wirelessly connected to a medication delivery device. While it is common for devices to connect wirelessly to form a system (e.g., a speaker connecting to a media source via BLUETOOTH®), there are specific challenges and concerns that arise in medication delivery, especially ambulatory medication delivery.

For example, for some conditions and therapies, a patient may need to carry an ambulatory medication delivery device (e.g., an infusion pump, injection pen, an inhaler, etc.) with them all times. Even if not necessary, many patients carry their drug delivery devices with them simply for convenience and risk aversion. So, a patient could take an ambulatory medication delivery device loaded with a dangerous medication, literally, anywhere in the world.

Opportunities for mis-delivery and dangerous consequences are higher when patients are being treated by a therapy system that includes a variety of therapy devices communicating with each other. For example, a patient may be treated by a therapy system that includes an analyte monitoring device, a therapy application executing on a mobile device, and a medication delivery device. In a typical operational cycle, the analyte monitoring device sends analyte measurement data to the therapy application. The therapy application performs therapy related analysis, determines changes to a medication therapy regime based on the analyte measurement data, and sends instructions to implement the changes to the medication delivery device. The medication delivery device reconfigures its medication delivery (e.g., dose amount, rate of dosing, etc.) based, at least in part, on the instructions.

If a third-party device (i.e., a therapy device that is not part of the therapy system) connects with any of the therapy devices that form the therapy system, that connection could interfere with the operation of the therapy system. The other device could be part of another therapy system, in which case the connection could interfere with operation of both therapy systems. So, even an inadvertent connection could cause information and instructions to be missed, or erroneous instructions to be sent. Moreover, the third-party device may be a malicious device that intends to capture therapy related information or even hijack operation of the therapy system and interfere with medication delivery (e.g., so called "main-in-the-middle" attacks).

Whether inadvertent or malicious, a misconnection and incorrect operation brings a significant risk of injury and death to users of therapy systems. The risk of an inadvertent or malicious connection are increased if the therapy devices are able to connect to each other and third-party devices using wireless communication links.

As used herein "a connection" and "connected" when used with references to two or more devices means that there is a communication link between two devices. The communication link may be wired, unwired (e.g., using wireless radio-frequency (RF) signals), and combinations thereof. "Connecting" means one or more operations are being taken to establish a communication link or a type of communication link, for example, operations to establish an intermediate communication link, which in turn may be used for performing one or more operations to establish a trusted communication link.

One way to restrict wireless connections is to configure devices to limit at least certain communication to a trusted connection. One of ordinary skill in the art would appreciate a number of ways to establish a trusted connection (when two devices form or have a trusted connection, that is also referred to herein as "pairing" and being "paired"), and one non-limiting example is: discovery, authentication, agreement on a communication protocol, sharing identifiers, agreement on an encryption scheme, and then agreement that the trusted connection is active.

Due to the risk of inadvertent connections and malicious connections, passwords and/or passkeys are often used when establishing trusted connections. For example, a user reads an N-digit code at a first device that is in a pairing mode, and enters the N-digit code at a second device that is in a pairing mode. The second device provides the N-digit code to the first device over a wired or wireless connection. If the first device determines that the displayed N-digit code matches the received N-digit code, then the first device approves the pairing and the first and second devices establish a trusted connection. The N-digit code is an example of a "shared secret," which is a piece of data, known only to parties involved in setting up the trusted connection. By way of example, a shared secret may be a password, a passphrase, a big number, an array of randomly chosen bytes, and the like. In some cases, both devices will store the shared secret and, periodically, the first device will ask the second device to again provide the shared secret to the first device in order to maintain the trusted connection.

Shared-secrets are effective, but as time passes, the risk that the shared secret will be compromised grows (e.g., a third-party might see the code displayed on the first device). Further, even with a shared secret, there is the risk of a brute force attack on the device where an attacker iterates through candidate passkeys until one is accepted.

Security risks aside, in the case of medication therapies, there are social and privacy drawbacks to current pairing techniques. For example, a user may be embarrassed to look at an analyte monitoring device and program a passkey into a medication delivery device in public because it exposes their health condition to strangers. If the devices are visible, that exposes the user to risk because a malicious actor may observe the user and target the user's devices, including in the manner described above. Further, physically reading a shared secret at the first device and entering it at the second device affects the user experience, and can cause a system that is supposed to reduce cognitive burden on a user to be more burdensome. Finally, the first device that provides the passkey must include a user interface sufficient to present the passkey to a user (e.g., a display, light-emitting-diodes, a speaker).

Accordingly, the inventors of this disclosure see a need for systems, methods, and devices that securely facilitate establishing trusted connections among therapy devices that form medication therapy systems.

FIG. 1 is a functional block diagram of a therapy system 100, which includes at least some therapy devices that are configured to establish trusted connections in accordance with one or more embodiments of the disclosure. Therapy system 100 is configured, generally, to monitor a patient and deliver therapeutic amounts of medication to the patient. In one or more embodiments, therapy system 100 includes an analyte monitoring unit 102, medication therapy electronics 104, a remote therapy management system 106, and a medication delivery unit 118.

In one or more embodiments, medication therapy electronics 104 is configured, generally, to analyze therapy related information, provide therapy recommendation to users, and send therapy instructions to medication delivery unit 118. Medication therapy electronics 104 is operatively coupled to medication delivery unit 118, and, in one or more embodiments, medication therapy electronics 104 and medication delivery unit 118 are components of a medication delivery device. In one embodiment, the medication delivery device may be a "smart" medication delivery device, where the medication therapy electronics 104 provides processing power related to the therapy as well as the user experience. For example, the medication delivery device may be an infusion pump system that is configured to automatically deliver medication based on control signals determined at the pump system (e.g., at the medication therapy electronics 104). By way of further example, the medication delivery device may be an injection pen that is configured to provide therapy recommendations based on detected delivery events and/or physiological information about a patient.

In another embodiment, medication therapy electronics 104 may be, or be a component of, a first device and medication delivery unit 118 may be, or be a component of, a second device. The first and second devices may be operatively coupled by a wired or wireless connection. In one embodiment, the connection may be a trusted connection established in accordance with one or more embodiments of the disclosure.

In one or more embodiments, medication therapy electronics 104 is configured to establish a trusted communication link with one or more therapy related devices, including analyte monitoring unit 102 and/or medication delivery unit 118. In one contemplated process for establishing a trusted communication link with analyte monitoring unit 102, medication therapy electronics 104 is configured to provide a candidate shared secret key 116 over an intermediate communication link 114a to analyte monitoring unit 102. In various embodiments, candidate shared secret key 116 may be a value or string of alpha-numeric characters representative of a candidate shared secret to be validated against a shared secret that is unique to analyte monitoring unit 102. In one or more embodiments, shared secrets and candidate shared secrets may be values, strings of alpha-numeric characters, algorithms, or combination thereof. In a contemplated operation of therapy system 100 candidate shared secret key 116 is used, but it is specifically contemplated that there may be multiple pairs of therapy related devices within a therapy system that use different unique shared secrets, candidate shared secrets, and candidate shared secret keys to establish trusted connections. In one embodiment, a shared secret may be unique to therapy system 100 (e.g., a therapy system identifier, algorithm, or combination thereof), and so the same shared secret, candidate shared secret, and candidate shared secret key may be used to establish trusted communication links between some or all of the therapy devices that comprise therapy system 100.

Turning back to the example of FIG. 1, in one or more embodiments, medication therapy electronics 104 provides candidate shared secret key 116 responsive to shared secret parameters that it requests and receives from remote therapy management system 106 over communication network 108. If analyte monitoring unit 102 accepts candidate shared secret key 116, or more specifically, if the analyte monitoring unit 102 verifies the candidate shared secret based, at least in part, on the candidate shared secret key 116, then a trusted communication link is established between analyte monitoring unit 102 and medication therapy electronics 104.

In one embodiment, establishing a trusted communication link includes recording at both devices that intermediate communication link 114a is a trusted communication link. In another embodiment, intermediate communication link 114a is ended and a new communication link 114b is established with trusted communication characteristics (e.g., protocol, encryption, etc.). In various embodiments, the trusted communication link 114b may use the same or different communication equipment (e.g., transceivers configured for BLUETOOTH®, ZIGBEE®, NFC, etc.) as intermediate communication link 114a.

In various embodiments, medication therapy electronics 104 may be configured to communicate over intermediate communication link 114a and trusted communication links, 114b as well as over communication network 108, and may include equipment for several types of communication.

In one or more embodiments, remote therapy management system 106 may execute on one or more computer servers remote from one or more other therapy devices, such as the medication therapy electronics 104, analyte monitoring unit 102, and medication delivery unit 118. The other therapy related devices may be carried with a user, while the remote therapy management system 106 operates remotely and provides services to devices within the therapy system 100.

In one embodiment, medication therapy electronics 104 sends a shared secret parameters request 112 to remote therapy management system 106. Remote therapy management system 106 receives shared secret parameters request 112 and sends response 110. Response 110 may include, for example, the requested shared secret parameters or a denial message denying the request 112. Medication therapy electronics 104 generates candidate shared secret key 116 responsive to shared secret parameters in the response 110.

Analyte monitoring unit 102 is configured to receive candidate shared secret key 116, and sends an acceptance or rejection message (not shown) over intermediate communication link 114a responsive to candidate shared secret key 116.

Figure 2:
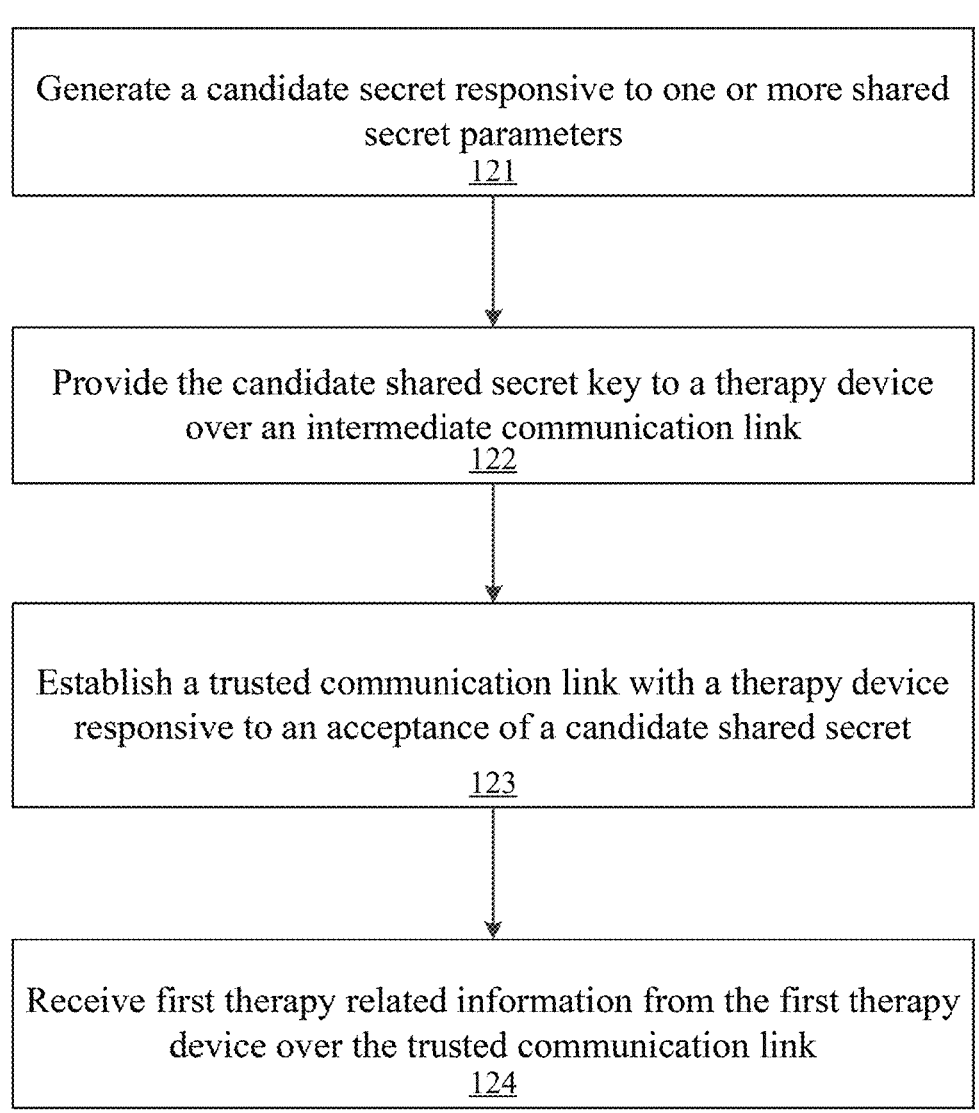
FIG. 2 is a flowchart of a process for establishing trusted communication links among therapy devices, in accordance with one or more embodiments of the disclosure.

FIG. 2 is a flowchart of a process 120 for establishing a trusted communication among therapy devices, in accordance with one or more embodiments of the disclosure. In operation 121, a candidate shared secret is generated responsive to one or more shared secret parameters. In operation 122, the candidate shared secret key is provided to a therapy device over an intermediate communication link. Candidate shared secret key is representative of one or more candidate shared secrets at a therapy device. In operation 123, a trusted communication link is established with a therapy device responsive to the therapy device accepting a candidate shared secret. In various embodiments and as described more fully herein, a candidate shared secret may be validated based, at least in part, on a candidate shared secret key. The trusted communication link is configured to enable communication of therapy related information from the first therapy device, so, in operation 124, first therapy related information is received from the first therapy device over the trusted communication link.

Figure 3A:
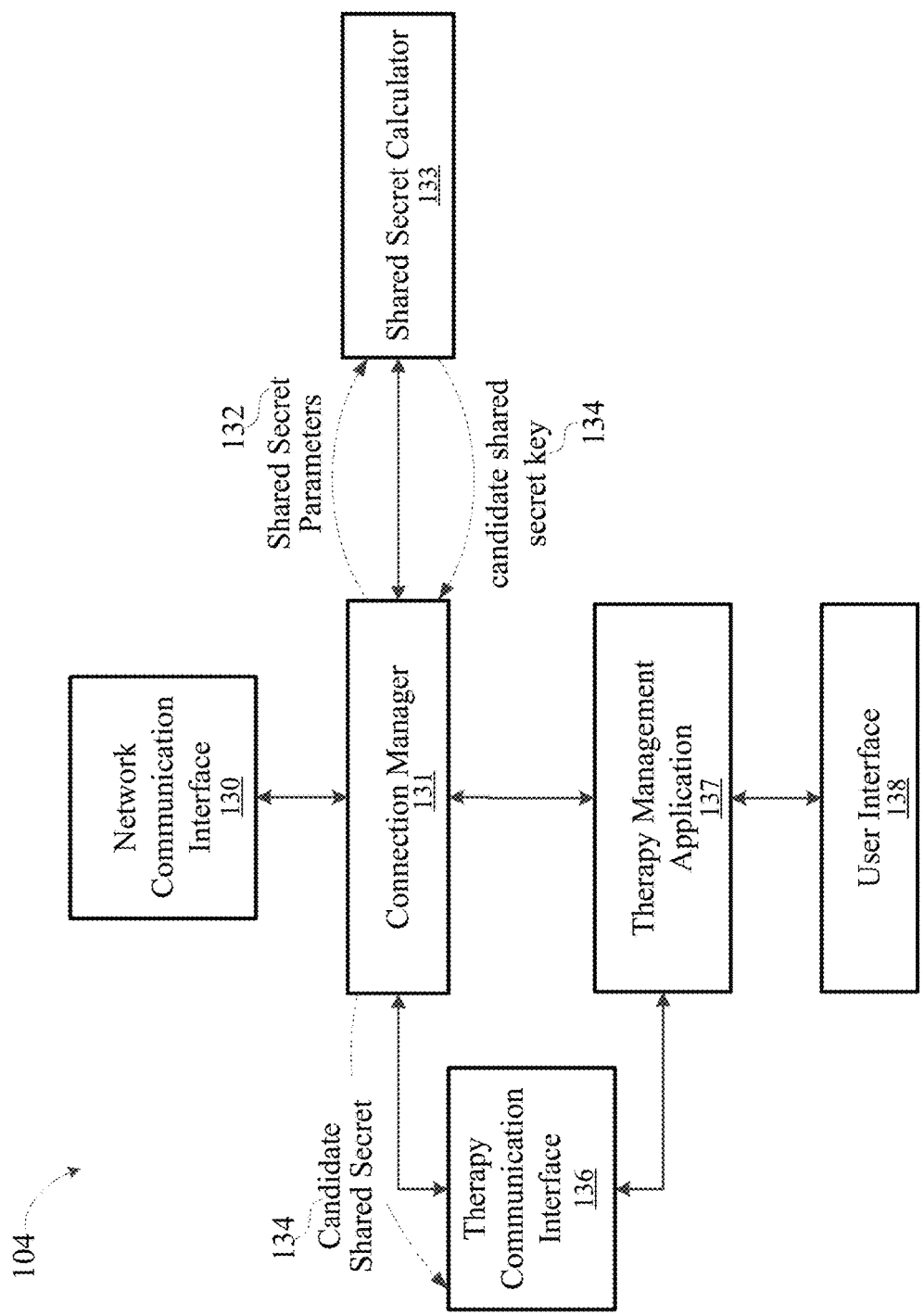
FIG. 3A is a functional block diagram of medication therapy electronics configured for establishing trusted communication links in accordance with one or more embodiments of the disclosure.

FIG. 3A is a functional block diagram of medication therapy electronics 104, in accordance with one or more embodiments of the disclosure. Medication therapy electronics 104 includes a connection manager 131, a shared secret key calculator 133, a therapy management application 137, and a user interface 138. Medication therapy electronics 104 also includes a network communication interface 130 and a therapy communication interface 136.

Connection manager 131 is configured, generally, to manage establishing one or more communication links with therapy related devices, including, for example, trusted and untrusted (e.g., intermediate) communication links. Connection manager 131 is configured to use network communication interface 130 to send shared secret parameter requests 112 from remote therapy management system 106 (FIG. 1), send one or more shared secret parameters 132 to shared secret key calculator 133 for processing, and to send candidate shared secret keys 134 from shared secret key calculator 133. Connection manager 131 is configured to receive candidate shared secret key 134 and provide candidate shared secret key 134 to a therapy related device (e.g., analyte monitoring unit 102 of FIG. 1) via therapy communication interface 136.

In one or more embodiments, network communication interface 130 may be configured to send requests to, and receive response messages from, remote therapy management system 106 (FIG. 1) over one or more networks, which may include, at least in part, the Internet. By way of example and not limitation, network communication interface 130 may be configured for wireless network communication (e.g., an IEEE 802.11 standard), cellular network communication (e.g., 3G, 4G LTE, 5G, CDMA, GSM etc.), microwave network communication, and combinations thereof.

Therapy communication interface 136 may be configured for personal, local, and/or wide-area network communication with a related therapy device. By way of example, and not limitation, therapy communication interface 136 may be configured for BLUETOOTH communication (including BLUETOOTH Low Energy (BLE)), NFC (near field communication), WiFi, ZIGBEE, IrDA (infrared data association), wireless USB (universal serial bus), combinations thereof, and more.

Shared secret key calculator 133 is configured to receive shared secret parameters 132 and provide candidate shared secret key 134. In one or more embodiments, shared secret key calculator 133 is configured to generate candidate shared secret key 134 responsive to shared secret parameters 132 and one or more secret operations. In one embodiment, shared secret key calculator 133 may be pre-configured to perform secret operations, and in another embodiment shared secret key calculator 133 may perform secret operations responsive to secret operation instructions that are included with the shared secret parameters 132.

In various embodiments, one or more shared secret parameters and/or secret operations may be a contemplated shared secret.

Figure 3B:
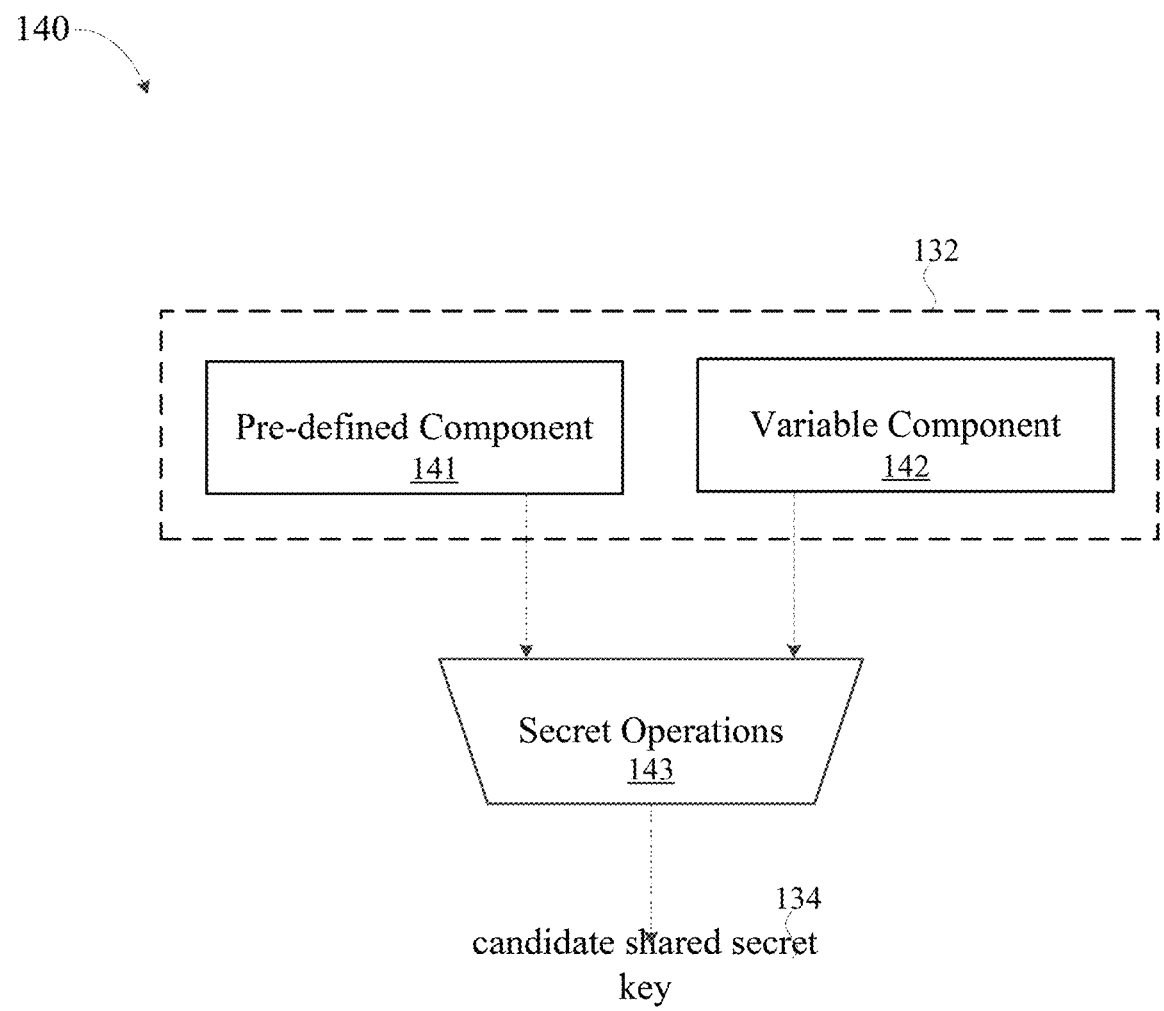
FIG. 3B is a flow chart of operations for determining a candidate shared secret key using a pre-defined component and a variable component, in accordance with one or more embodiments of the disclosure.

FIG. 3B shows a flow chart of a shared secret calculation process 140, in accordance with one or more embodiments of the disclosure. Secret operations 143 are performed responsive to a pre-defined component 141 and a variable component 142. In one embodiment, pre-defined component 141 may be a unique identifier that is associated with the therapy related device with which a trusted communication link is being established. By way of example, unique identifier may be a serial number that is associated with the therapy related device at manufacture or an identifier generated by a remote therapy system. Variable component 142 may be non-static, that is, it may change each time the shared secret calculation process 140 is performed. By way of example, variable component 142 may be time-based—e.g., a time (e.g., "4:28:09") or calculated using a specific time (e.g., "4:28:09"→4×28×09=1008). If calculated using a specific time, that time may be stored (e.g., in a time stamp format) and sent with the candidate shared secret key 134.

In one embodiment, pre-defined component 141 and variable component 142 are both received by shared secret key calculator 133 (see FIG. 3A) as part of shared secret parameters 132. In another embodiment, shared secret key calculator 133 may be include a variable component calculation module (e.g., a clock circuitry, calculation circuitry, random number generator, etc.) configured to generate variable component 142.

In one or more embodiments, secret operations 143 may be a one-way function configured to obfuscate its input parameters (e.g., pre-defined component 141 and variable component 142). Secret operations 143 may be performed using pre-defined component 141 and variable component 142. In one embodiment, each of pre-defined component 141 and variable component 142 may be a parameter of secret operations 143. In another embodiment, secret operations 143 may use a post-processed parameter that is based, at least in part, on pre-defined component 141 and variable component 142 (e.g., a combination of the two parameters using concatenation, exclusive OR, multiplication, etc.).

In one or more embodiments, secret operations 143 is a hashing function, shared secret parameters 132 is a hash key, and candidate shared secret key 134 is a hash. Shared secret key calculator 133 is configured to generate the hash by hashing the hash key using the hashing function. By using both the pre-defined component 141 and variable component 142, a correct candidate shared secret key 134 is harder to recover illicitly without knowing how the variable component affects secret operations 143.

In one or more embodiments, therapy management application 137 (see FIG. 3A) may be configured, generally, to receive therapy related information (e.g., analyte measurements), and provide one or more of therapy recommendations and therapy instructions. User interface 138 may be configured to provide therapy recommendations generated by therapy management application 137 to a user and receiver user input. In one or more embodiments, user interface 138 may be a graphical user interface presentable at a display operably coupled to medication therapy electronics 104 (see FIG. 1), that is configured to present therapy recommendations and/or therapy related information to a user. By way of example, and not limitation, therapy related information may include notifications, alarms, alerts, combinations thereof, and more. Therapy recommendations may include one or more of changes to medication dosing parameters, recommended bolus doses, recommended correction doses, dietary recommendations (e.g., to eat), physiological recommendations (e.g., sleep or exercise) and more. User input may include approvals, acknowledgements, dismissals, information about therapy relevant events, physiological information, parameters for medication therapies, and more.

Figure 4:
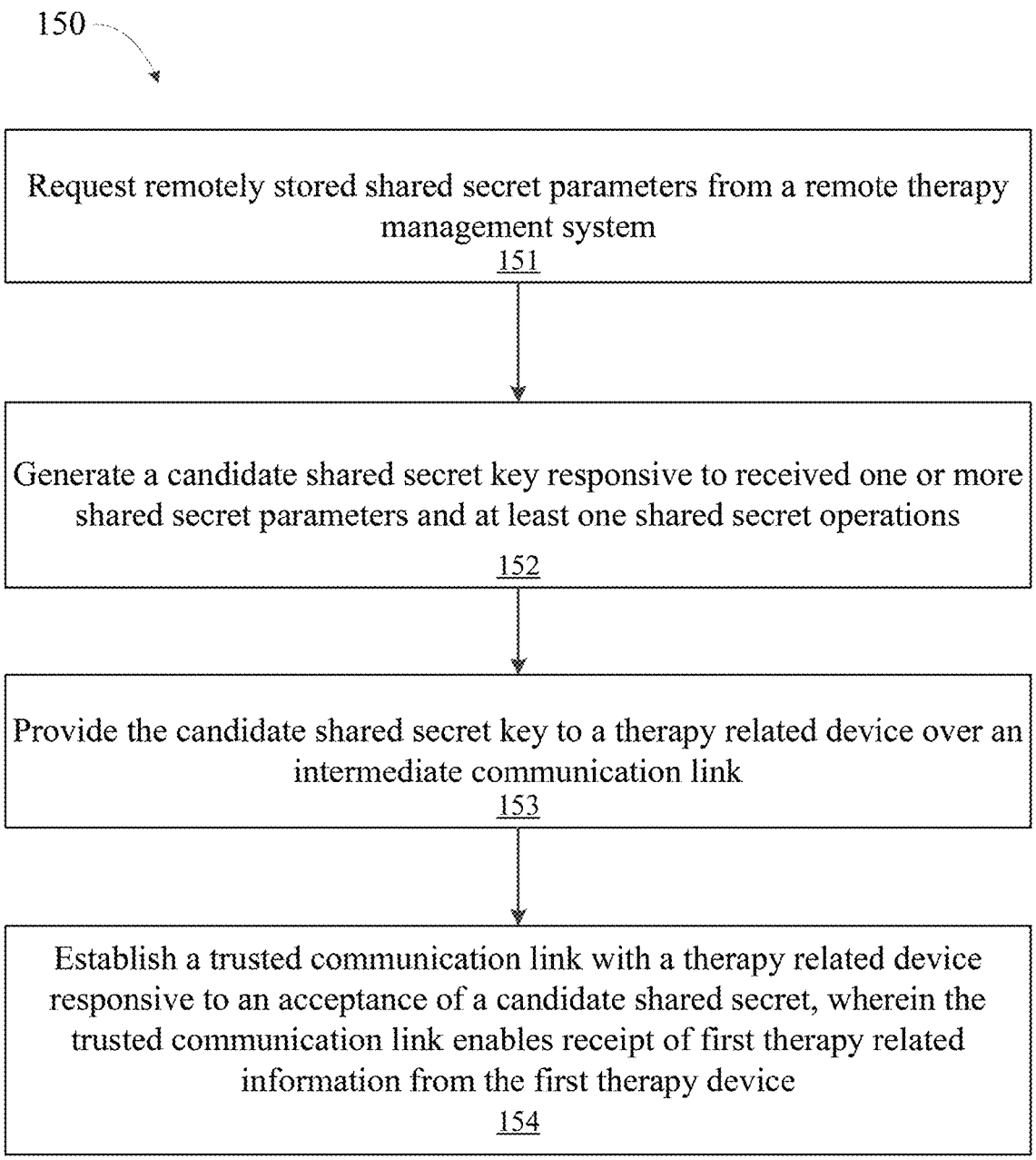
FIG. 4 is a flowchart of a process for establishing a trusted communication link with another therapy related device, in accordance with one or more embodiments of the disclosure.

FIG. 4 shows a flowchart of a process 150 for establishing a trusted communication link with another therapy related device, in accordance with one or more embodiments of the disclosure. In one or more embodiments, operations of process 150 may be performed at medication therapy electronics 104 (see FIG. 1), and is one contemplated operation of medication therapy electronics 104. In operation 151, remotely stored shared secret parameters are requested from a remote therapy management system. In one embodiment, shared secret parameters are received in a reply message from the remote therapy system. If the remote therapy management system rejects the request or fails to find the requested shared parameters, a reply message may be received indicating that the request was rejected or the system failed. In operation 152, a candidate shared secret key is generated responsive to received one or more shared secret parameters and at least one shared secret operation. The shared secret parameters may be a unique identifier, and, in one embodiment, may include a variable component as described in this disclosure. Shared secret operations may be locally stored or may be remotely stored and received with the shared secret parameters. In operation 153, a candidate shared secret key is provided to the therapy related device. The candidate shared secret key may be provided over an intermediate communication link. By way of example, the intermediate communication link may be an untrusted communication link, a temporary communication link used for establishing a trusted communication link, or a combination thereof. In operation 154, a trusted communication link is established with the therapy related device responsive to an acceptance of a candidate shared secret. The trusted communication link enables receipt of therapy related information from the therapy related device.

Figure 5:
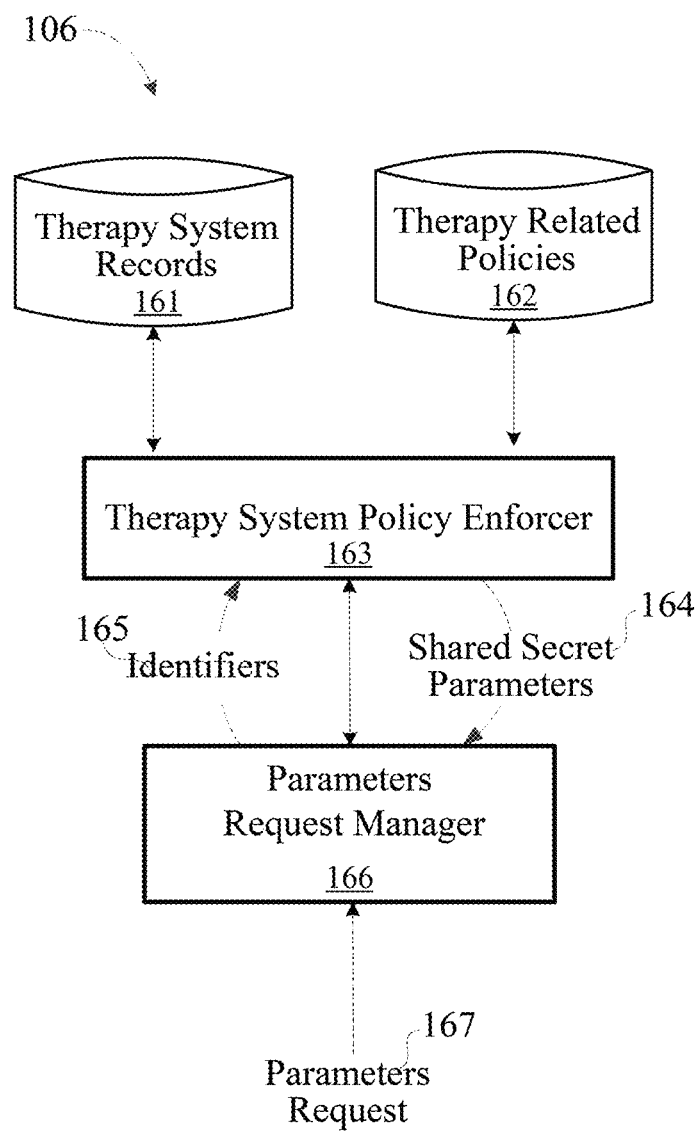
FIG. 5 is a functional block diagram of a remote therapy management system, in accordance with one or more embodiments of the disclosure.

FIG. 5 shows a functional block diagram of remote therapy management system 106, in accordance with one or more embodiments of the disclosure. Remote therapy management system 106 is configured, generally, to manage records related to therapy system 100 (see FIG. 1) and monitor aspects of operation of therapy system 100 and therapeutic delivery of medication more generally. In one or more embodiments, remote therapy management system 106 is configured to monitor and manage therapy system 100 responsive to one or more therapy related policies 162. Therapy related policies 162 may include, for example, restrictions on the number and kinds of therapy related devices that may be part of therapy system 100, as well as physical and operational requirements (e.g., security, updates, etc.) for therapy related devices that may be part of therapy system 100.

In one or more embodiments, remote therapy management system 106 may include a parameters request manager 166, a therapy system policy enforcer 163, therapy system records 161, and therapy related policies 162.

In one or more embodiments, parameters request manager 166 may be configured, generally, to manage parameter requests 167 for shared secret parameters received from therapy related devices that are attempting to establish trusted communication links. In one embodiment, parameter request manager 166 may be configured to provide one or more group identifiers 165 to therapy system policy enforcer 163 responsive to receiving a parameter request 167 for shared secret parameters. Group identifiers 165 may be unique identifiers that describe one or more groups of therapy related devices that form medication therapy system. In one embodiment, a group identifier 165 may be a string of digits or characters. In another embodiment, a group identifier 165 may be a patient's name or a string associated with a patient's name (e.g., an anonymizing identifier). In one embodiment, group identifiers 165 may for one or more of the therapy related devices that are attempting to establish a trusted communication link.

Therapy system policy enforcer 163 may be configured, generally, to enforce therapy related policies 162. More particularly, therapy system policy enforcer 163 may be configured to enforce therapy related policies 162 related to forming medication therapy systems from a group of therapy related devices, and more specifically still, to establishing trusted communication links among therapy related devices. So, when a therapy related device requests shared secret parameters, therapy system policy enforcer 163 may be configured to determine whether establishing a trusted communication link would violate one or more therapy related policies 162. For example, if the requesting therapy related device is attempting to establish a trusted communication link with an analyte monitoring unit, therapy system policy enforcer 163 may be configured to reject the request if the therapy system records 161 indicate that the requesting therapy related device already has an active trusted communication link with another, different, analyte monitoring unit. By way of another example, if the requesting therapy related device is attempting to establish a trusted communication link with an analyte monitoring unit, therapy system policy enforcer 163 may be configured to reject the request if the therapy system records 161 indicate that the analyte monitoring unit already has an active trusted communication link with another, different, therapy related device or has reached a maximum number of active trusted communication links with other, different, therapy related devices. By way of yet another example, if the requesting therapy related device is attempting to establish a trusted communication link with an analyte monitoring unit, therapy system policy enforcer 16 may be configured to reject the request if the requesting therapy related device and the other therapy related device are not compatible. For example, therapy related policies 162 may describe lists of compatible types of devices (or, conversely, lists of incomputable devices), and if the requesting therapy related device and the other therapy related device are not compatible then therapy system policy enforcer 16 may be configured to reject the request.

In the contemplated example of FIG. 5, if therapy system policy enforcer 163 determines that the trusted communication link would not violate one or more of therapy related policies 162, then it may retrieve the shared secret parameters responsive to group identifiers 165, therapy system records 161, and the policy determination. Therapy system policy enforcer 163 may provide the shared secret parameters 164 to parameters request manager 166, which in turn may generate and send a reply message to the requesting therapy related device, and the reply message may include shared secret parameters 164. If the request is rejected or fails (e.g., because no relevant therapy system records 161 may be found responsive to group identifiers 165), then the reply message may indicate the rejection or failure.

Therapy system records 161 may include records stored in a database that are related to one or more medication therapy systems. Therapy system records 161 may describe therapy related devices that form a medication therapy system, including identifiers, type of devices, patient information, insurance information, provider information, and more.

FIG. 6 is a flowchart of a process 170 for enforcing policies for establishing trusted communication links among therapy devices, in accordance with one or more embodiments of the disclosure. In one or more embodiments, operations of process 170 may be performed at remote therapy management system 106, and is one contemplated operation of remote therapy management system 106. In operation 171, a request for shared secret parameters is received. The request may be received from a first therapy device that is attempting to establish a trusted communication link with a second therapy device. In operation 172, a reply message is sent responsive to the request for shared secret parameters. The contents of the reply message may be selected responsive to one or more therapy system policies and/or searches of therapy system records, and may include, for example, shared secret parameters or a denial message. The therapy system policies and therapy system records may be managed at one or more databases. Therapy system policies may describe restrictions that apply to therapy devices and groups of therapy devices. Therapy system records may describe individual therapy devices and groups of therapy devices that form medication therapy systems.

Figure 7:
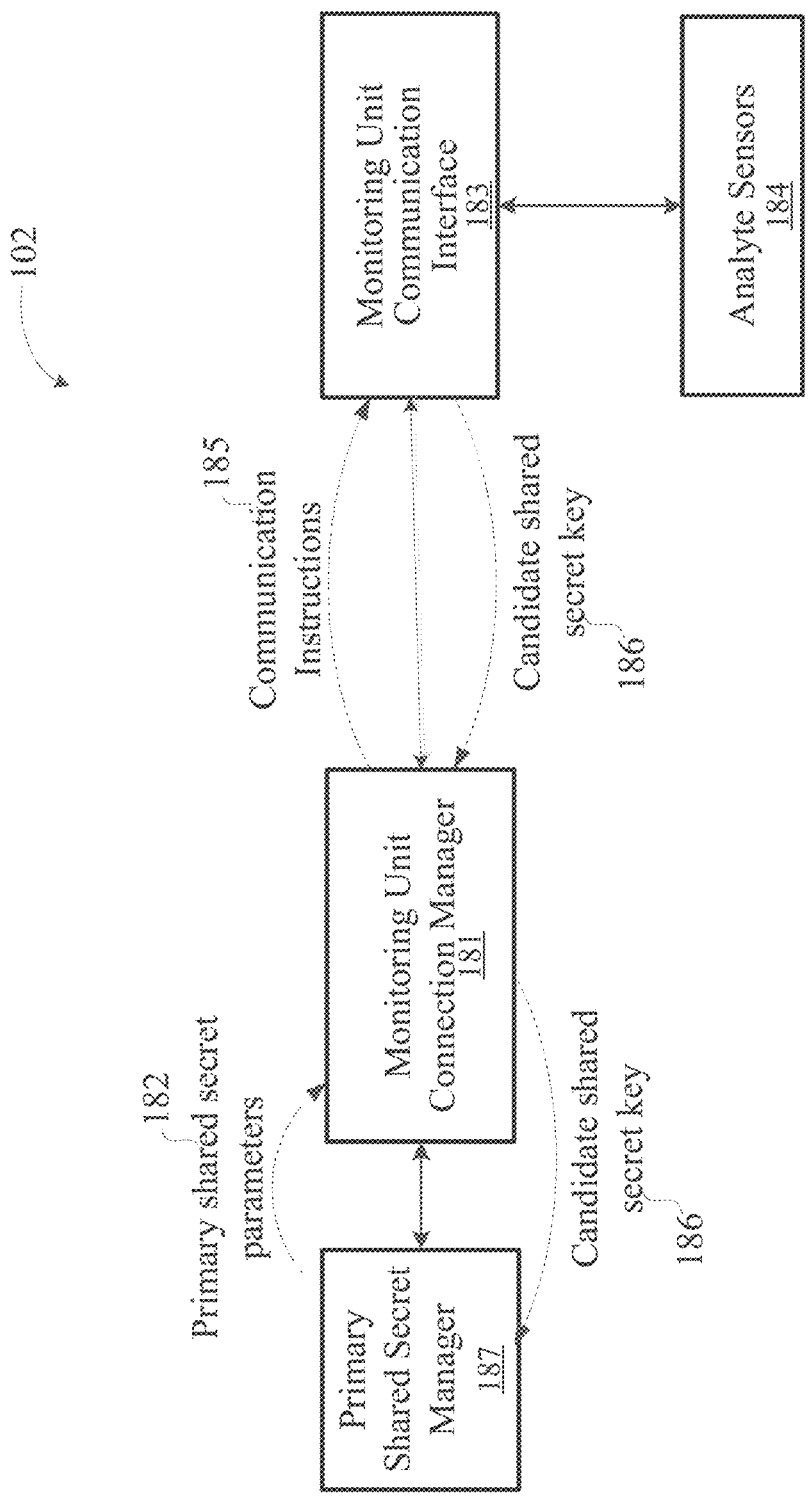
FIG. 7 is a functional block diagram of an analyte monitoring unit configured for establishing trusted communication links, in accordance with one or more embodiments of the disclosure.

FIG. 7 is a functional block diagram of analyte monitoring unit 102, in accordance with one or more embodiments of the disclosure. Analyte monitoring unit 102 is configured, generally, to measure analyte levels in blood samples and send the measurements to therapy related devices that, together with analyte monitoring unit 102, may be part of a medication therapy systems. One or more embodiments of analyte monitoring unit 102 may include a monitoring unit connection manager 181, a monitoring unit communication interface 183, and analyte sensors 184.

Monitoring unit communication interface 183 is configured, generally, to send and receive messages to and from other therapy related devices, for example, over trusted and/or untrusted communication links. In one or more embodiments, messages sent by monitoring unit communication interface 183 may include one or more of analyte measurement information received from analyte sensors 184, and status information about analyte monitoring unit 102 (e.g., battery life, component health, etc.). Monitoring unit communication interface 183 may also be configured to send and receive messages related to establishing trusted communication links with other therapy related devices.

Monitoring unit connection manager 181 is configured, generally, to manage establishment of trusted communication links with other therapy related devices. Monitoring unit connection manager 181 may include or have access to primary shared secrets 182 stored at analyte monitoring unit 102. In a contemplated operation of analyte monitoring unit 102, when a therapy device attempts to establish a trusted communication link with analyte monitoring unit 102, monitoring unit connection manager 181 is configured to validate a candidate shared secret responsive to candidate shared secret key 186 and primary shared secrets 182.

In one or more embodiments, primary shared secret manager 187 is configured to generate and provide primary shared secret parameters 182 to monitoring unit connection manager 181. In one embodiment, primary shard secret manager 187 stores one or more primary shared secret parameters that it provides to connection manager 181. In one contemplated operation, the primary shared secret parameters may include a unique identifier (e.g., a string of alpha numeric characters), a decryption key, and an encrypted string (e.g., cyphertext) that was generated based, at least in part, on the unique identifier, an encryption algorithm corresponding to the decryption algorithm, and an encryption key. Connection manager 181 may decrypt the encrypted string using the decryption algorithm and the candidate shared secret key 186. In a contemplated operation, if the decrypted string matches the unique identifier than that is indicative that a candidate shared secret matches a primary shared secret of the analyte monitoring unit 102. The primary shared secret may be a unique identifier, a hash function, or both.

In another embodiment, primary shared secret parameters 182 may be a primary shared secret key generated by primary shared secret manager 187. Primary shared secret manager 187 may perform secret operations with a unique identifier to generate a primary key, and provide the primary key to connection manager 181 to compare the primary key to candidate shared secret key 186. In a case where candidate shared secret key 186 matches the primary key then that is indicative that the primary secret operations and primary shared secret parameters are the same as the ones used to generate candidate shared secret key 186. For example, the secret operations performed at primary shared secret manager 187 may be the same hashing function or other one-way function performed at shared secret key calculator 133 (see FIG. 3A). In a case where candidate shared secret key 186 does not match a primary key, then any of the secret operations and shared secret parameters may be different than those used to generate candidate shared secret key 186.

Any suitable technique known by one of ordinary skill in the art may be used by monitoring unit connection manger 181 to perform comparisons described herein. For example, a symbol-to-symbol comparison, bit-to-bit comparison, converting to an integer (e.g., if they are strings) and comparing integer values, and the like.

FIG. 8 is a flowchart of a process 190 for establishing trusted communication links with a therapy device, in accordance with one or more embodiments of the disclosure. In one or more embodiments, operations of process 190 may be performed at analyte monitoring unit 102 (see FIG. 1 and/or FIG. 7). In operation 191, an intermediate communication link is established with a therapy device that is attempting to establish a trusted communication link. In operation 192, a request for a shared secret is sent to the therapy device over the intermediate communication link. In operation 193, a candidate shared secret key is received from the therapy device over the intermediate communication link. In one embodiment, a countdown is implemented and if the candidate shared secret key is not provided within a certain amount of time, the request "times out" and a candidate shared secret is automatically rejected. This avoids a problem whereby the requesting therapy device is waiting in an active intermediate mode, which may happen if the requesting therapy device fails to receive shared secret parameters from a remote therapy management system. In operation 194, a candidate shared secret is validated responsive to a primary shared secret. In various embodiments, the primary shared secret or values indicative of it may be stored or calculated locally. In operation 195, a trusted communication link is established with the requesting therapy device responsive to the comparison. For example, if a candidate shared secret matches a primary shared secret then an acceptance message is provided to the requesting therapy device. If a candidate shared secret does not match a primary shared secret then a rejection message is provided to a requesting therapy device. Once the trusted communication link is established, therapy related information may be sent between therapy devices. For example, analyte monitoring unit 102 may send analyte measurement data 326 to a therapy related device that includes without limitation medication therapy electronics 104.

One or more embodiments relate, generally, to a process for establishing trusted connections that may be performed by therapy devices using shared secrets stored or determined locally, and systems and devices for accomplishing the same.

Figure 9:
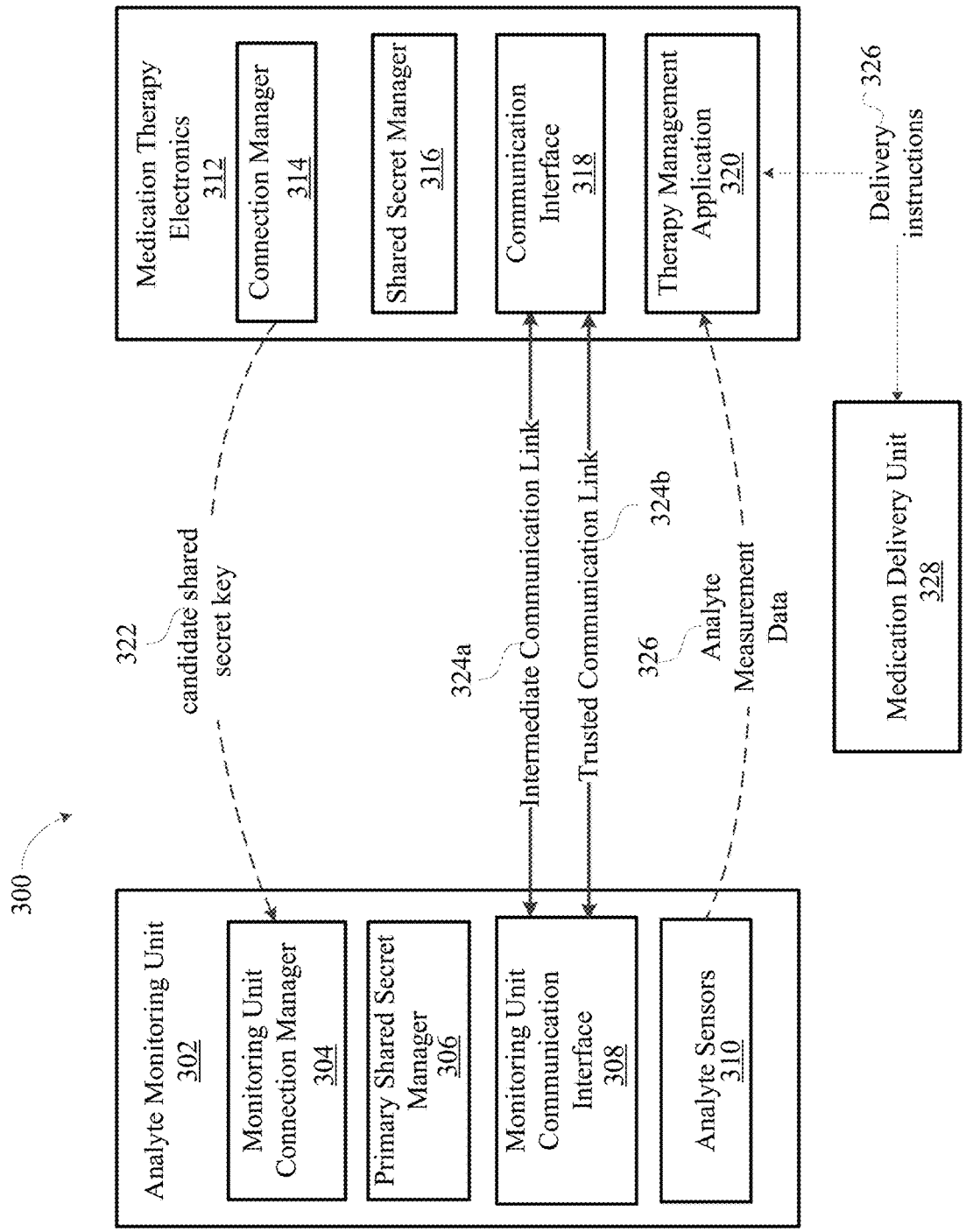
FIG. 9 shows a functional block diagram of a therapy system that includes at least some therapy devices that are configured to establish trusted connections in accordance with one or more embodiments of the disclosure.

FIG. 9 is a functional block diagram of therapy system 300 that includes at least some therapy devices that are configured to establish trusted connections in accordance with one or more embodiments of the disclosure. Therapy system 300 is configured, generally, to monitor a patient and deliver therapeutic amounts of medication to the patient. In one or more embodiments, therapy system 300 includes an analyte monitoring unit 302, medication therapy electronics 312, and a medication delivery unit 328.

Notably, a remote therapy system is not shown as part of therapy system 300 because, in one or more embodiments, medication therapy electronics 312 is configured to store and/or calculate the shared secret locally. Nevertheless, one of ordinary skill in the art would understand that therapy system 300 may include remote therapy management elements.

In one or more embodiments, medication therapy electronics 312 includes a connection manager 314, a shared secret manager 316, a communication interface 318, and a therapy management application 320. In one embodiment, shared secret manager 316 is configured to retrieve a locally stored candidate shared secret key 322 responsive to a request to provide a shared secret from analyte monitoring unit 302, and connection manager 314 is configured to provide candidate shared secret key 322 to analyte monitoring unit 302. Candidate shared secret key 322 may be, for example, a hash of a unique identifier associated with analyte monitoring unit 302.

In one or more embodiments, shared secret manager 316 is configured to determine candidate shared secret key 322. In one embodiment, a secret and one or more secret operations are stored at medication therapy electronics 312. By way of example, the secret may be a hash key and the secret operations may be a hashing function. Shared secret manager 316 determines candidate shared secret key 322 by performing secret operations using secrets as a parameter.

In one or more embodiments, a secret may be static, for example, it may be a unique identifier associated with analyte monitoring unit 302. In one or more embodiments, the secret operations may be configured to use at least two parameters: a static component (e.g., a unique identifier) and a variable component (e.g., a time), such that the candidate shared secret key 322 is different for different variable components. In yet another embodiment, the secret may be a combination of a unique identifier and a variable component.

In one or more embodiments, analyte monitoring unit 302 may include monitoring unit connection manager 304, primary shared secret manager 306, monitoring unit communication interface 308, and analyte sensors 310. Monitoring unit connection manager 304 is configured to validate a candidate shared secret based, at least in part, on candidate shared secret key 322 responsive to a primary shared secret provided by primary shared secret manager 306, for example, by comparing candidate shared secret key 322 to a primary shared secret or a primary shared secret key generated using a primary shared secret.

In one embodiment, analyte monitoring unit 302 may store a primary shared secret. In another embodiment, primary secret parameters and secret operations may be stored at analyte monitoring unit 302, and primary shared secret manager 306 may be configured to determine a primary shared secret or a primary shared secret key, at least in part, using secret operations. In the example of FIG. 8, if secret operations and a secret key used by primary shared secret manager 306 are the same as secret operation(s) and a secret key(s) used by shared secret manager 316 of medication therapy electronics 312 to generate candidate shared secret key 322, then primary shared secret key will match candidate shared secret key 322. If a candidate shared secret is validated at least in part using candidate shared secret key 322, then analyte monitoring unit 302 is configured to send an acceptance message to medication therapy electronics 312, and the two devices may establish trusted communication link 324*b*.

Notably, candidate shared secret key 322 may also include a variable component if used to generate it, for example, a time stamp. Primary shared secret manager 306 may generate a primary shared secret or primary shared secret key responsive to a variable component, primary secret operations, and primary shared secret parameters.

FIG. 10 is a flowchart of a process 330 for establishing a trusted communication link with another therapy related device, in accordance with one or more embodiments of the disclosure. In one or more embodiments, operations of process 330 may be performed at medication therapy electronics 312, and is one contemplated operation of medication therapy electronics 312. In operation 332, a candidate shared secret key is generated responsive to one or more locally stored shared secret parameters and locally stored shared secret operations. In various embodiments, the shared secret parameters may include static components, variable components, and/or secret operations. In operation 334, a candidate shared secret key is provided to a therapy related device over an intermediate communication link 324*a*. In operation 336, a trusted communication link is established with the therapy related device responsive to an acceptance of a candidate shared secret. Acceptance may be communicated responsive to validating a candidate share secret using a candidate shared secret key. In one or more embodiments, a trusted communication link is configured to enable receipt of therapy related information from the therapy device.

One or more embodiments of the disclosure relate to insulin therapy systems configured to implement pairing techniques described in this disclosure.

Diabetes mellitus is a chronic metabolic disorder caused by the inability of a person's pancreas to produce sufficient amounts of the hormone insulin such that the person's metabolism is unable to provide for the proper absorption of sugar and starch. This failure leads to hyperglycemia, i.e., the presence of an excessive amount of glucose within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to constantly maintain the level of blood analyte within normal limits. Such glycemic control is achieved by regularly supplying external drugs to the body of the patient to thereby reduce the elevated levels of blood analyte.

An external biologically effective drug (e.g., insulin or its analog) is commonly administered by means of daily injections. In some cases, multiple, daily injections (MDI) of a mixture of rapid- and long-acting insulin via a reusable transdermal liquid dosing device (commonly referred to as an "insulin pen") or a hypodermic syringe. The injections are typically administered by a person with diabetes (PWD), and so requires self-monitoring of blood glucose and the self-administration of insulin. The PWD that manages their care using MDI often plans insulin injections for each day, in advance, based on basal insulin requirement as well as external factors such as meals, exercise, sleep, etc. A typical dosing plan will include the time of day for an injection, the type of insulin (e.g., fast acting, long acting, a mixture of fast acting and long acting, etc.), and amount of insulin for each dose. In addition, PWDs will self-monitor their blood glucose and self-administer "bolus" dose(s) of rapid-acting insulin if their blood glucose is too high or consume carbohydrates (or sometimes administer glycogen) if their blood glucose is too low.

The "correct" insulin dose is a function of the level of glucose in the blood, physiological factors such as a person's insulin sensitivity, and lifestyle factors such as meals (e.g., recently consumed carbohydrates that have yet to be metabolized into glucose and absorbed into the blood). Moreover, even with careful planning and self-monitoring, a PWD may skip doses, double dose, and dose the wrong amount and/or type of insulin. Insufficient insulin can result in hyperglycemia, and too much insulin can result in hypoglycemia, which can result in clumsiness, trouble talking, confusion, loss of consciousness, seizures, or death. Accordingly, PWDs face a considerable cognitive burden in determining appropriate doses of insulin.

In order to assist with self-treatment, some insulin therapy devices (e.g., blood glucose meters, continuous glucose meters, insulin pumps, insulin pens etc.) are equipped with insulin therapy applications that assist user with making appropriate therapy decisions while minimizing the burdens of data entry, mental calculations, procedures, etc.). For example, insulin bolus calculators may be used that have the user input an estimate (e.g., numerical estimate) of the quantity of carbohydrates consumed or about to be consumed (or additionally or alternatively protein, fat, or other meal data) and the bolus calculator outputs a recommended size for the insulin bolus dosage. Although bolus calculators remove some of the mental calculations that need to be made by the user in determining an appropriate insulin bolus dosage, bolus calculators still burden the user with the mental task of evaluating the constituents of their meal, may require the use of a secondary device, and often require manual entry of data.

Automated insulin delivery may also be used to relieve some of the burdens of self-treatment. A glucose monitoring unit measures levels of glucose in blood samples and sends at least some of the measurements to a therapy application that is monitoring patient's response to insulin therapy. The therapy application determines insulin dosing (e.g., amount, timing, rates of insulin, etc.) dosing to account for a patient's basal insulin needs as well as to account for physiological events such as carbohydrate intake, exercise, sleep, medication intake (other than insulin), and more. The therapy application uses glucose levels received from the glucose monitoring unit as a control variable to determine insulin dosing instructions that it then sends to an insulin delivery device, such an infusion pump. The operation of the insulin delivery device is configured by the insulin dosing instructions and the insulin delivery device will then deliver insulin according to the new configuration. Insulin therapy systems that implement automated insulin delivery may operate in "open loop" modes and "closed loop" modes. By way of example, in an open loop mode, the insulin therapy system may involve some user interaction before sending the insulin delivery instructions 326 to the insulin delivery device (e.g., a user acceptance of change). In a closed loop mode, the therapy application may determine and automatically send the insulin delivery instructions 326 to the insulin delivery device without user interaction.

Figure 11:
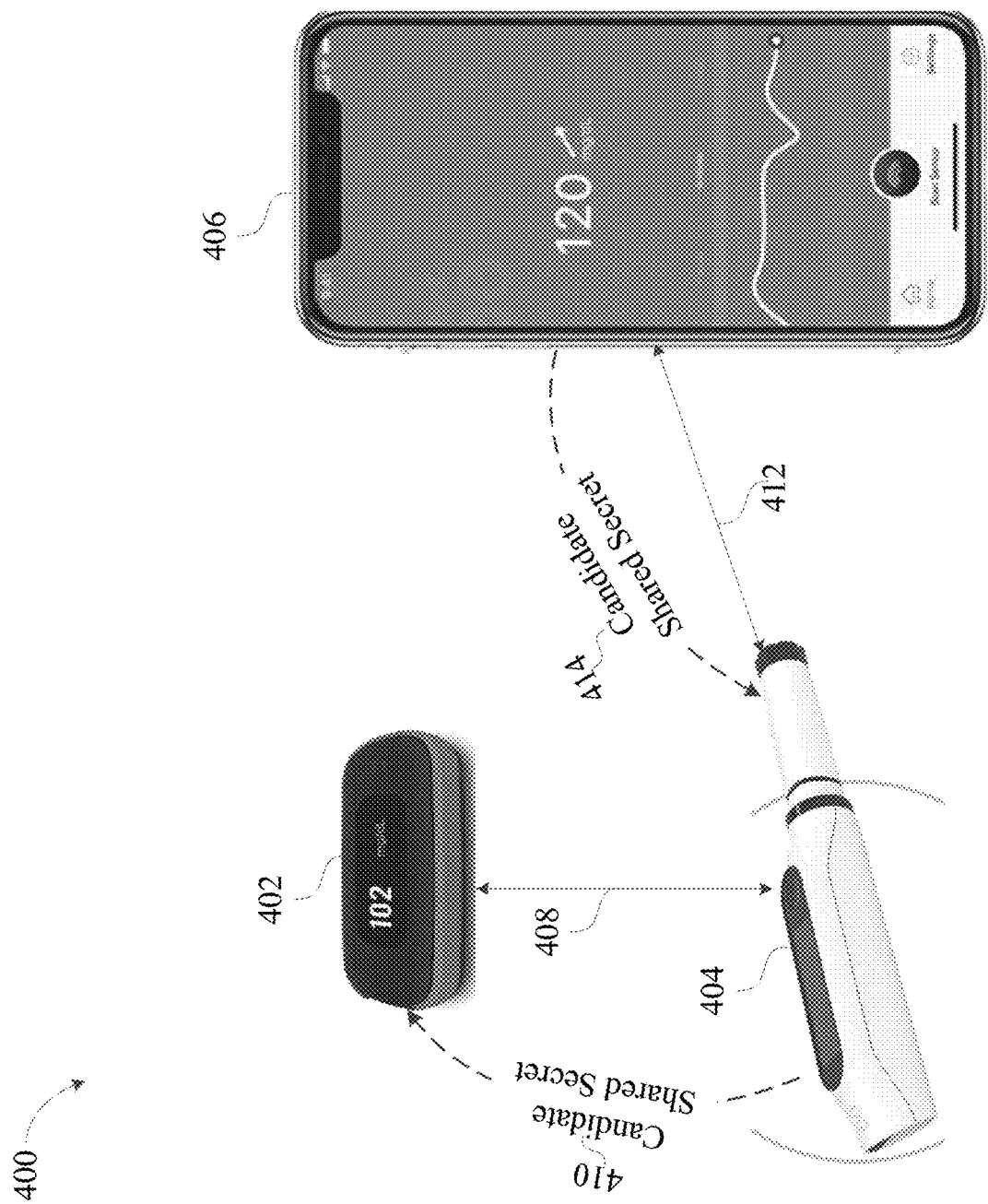
FIG. 11 shows an insulin therapy system configured for pairing therapy devices in accordance with one or more embodiments of the disclosure.

FIG. 11 shows an insulin therapy system 400 configured for pairing in accordance with one or more embodiments of the disclosure. Insulin therapy system 400 includes a blood glucose meter (BGM) 402, an insulin injection pen 404, and a mobile computing device 406 with an insulin therapy application executing thereon.

In one or more embodiments, insulin injection pen 404 and BGM 402 are configured for pairing in accordance with the embodiments for establishing a trusted communication link described in this disclosure. In one embodiment, a shared secret is locally stored at BGM 402, and upon request, insulin injection pen 404 is configured to provide a candidate shared secret to BGM 402 in order to pair with BGM 402 and start receiving glucose level measurement data from BGM 402. If insulin injection pen 404 fails to provide candidate shared secret 410 or BGM 402 does not validate candidate shared secret 410 (e.g., using its stored primary shared secret, or using a shared secret key and secret operations), pairing will fail and trusted communication link 408 will not be established.

In one or more embodiments, mobile computer device 406 and insulin injection pen 404 are configured for pairing in accordance with the embodiments for establishing a trusted communication link described in this disclosure. In one embodiment, a shared secret is locally stored at insulin injection pen 404, and upon request, mobile computing device 406 is configured to provide a candidate shared secret 414 in order to pair with insulin injection pen 404 and start receiving insulin dosing event information from insulin injection pen 404. If mobile computing device 406 fails to provide candidate shared secret 414 or if insulin injection pen 404 does not validate candidate shared secret 410 against its stored primary shared secret, pairing will fail and trusted communication link 412 will not be established.

Figure 12:
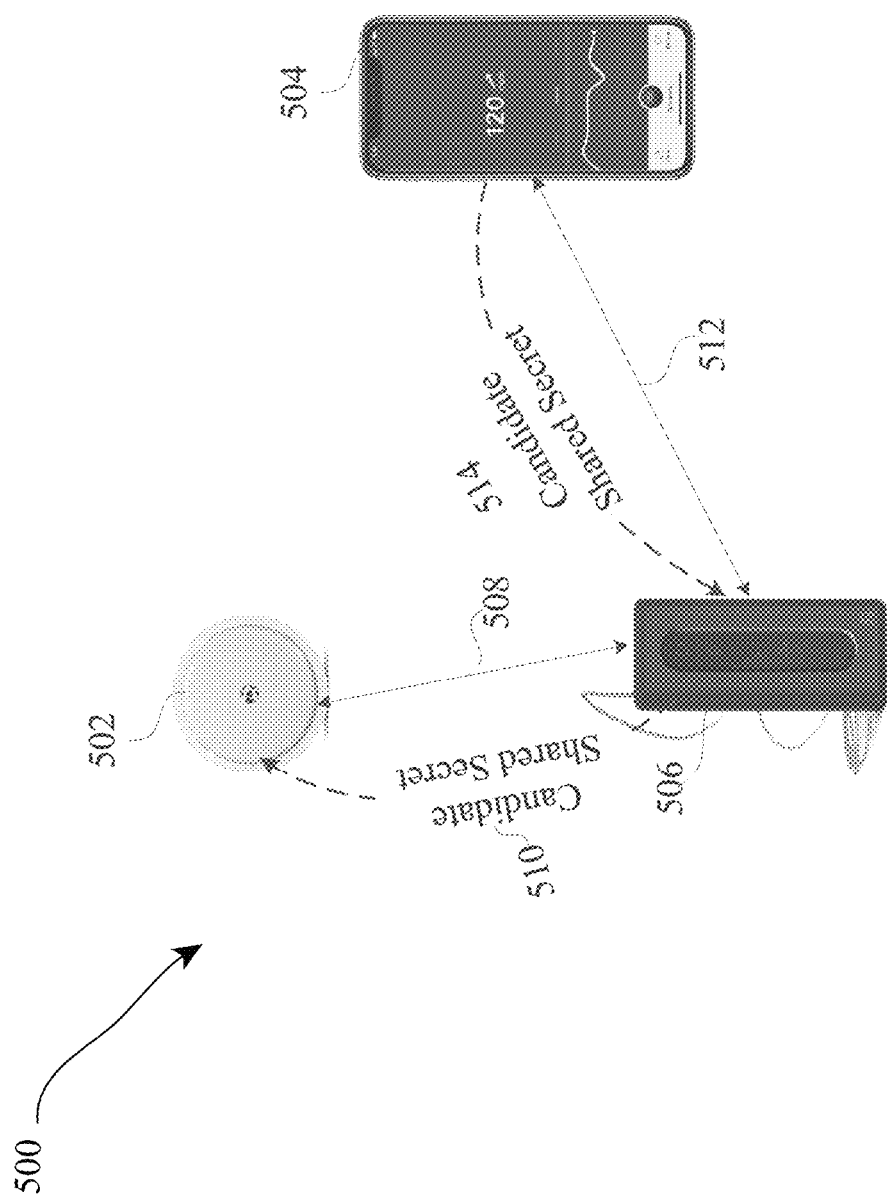
FIG. 12 shows an automated insulin therapy system configured for pairing therapy devices in accordance with one or more embodiments of the disclosure.

FIG. 12 shows an automated insulin therapy system 500 configured for pairing in accordance with one or more embodiments of the disclosure. Automated insulin therapy system 500 includes a continuous glucose monitor (CGM) 502, an insulin infusion pump 506, and a mobile computing device 504 with an insulin therapy application executing thereon. Automated insulin therapy system 500 may be configured for open loop and closed loop delivery of insulin to a patient.

In one or more embodiments, insulin infusion pump 506 and CGM 502 are configured for pairing in accordance with the embodiments for establishing a trusted communication link described in this disclosure. In one embodiment, a shared secret is locally stored at CGM 502, and upon request, insulin infusion pump 506 is configured to provide a candidate shared secret 510 to CGM 502 in order to pair with CGM 502 and start receiving glucose level measurement data from CGM 502. If insulin infusion pump 506 fails to provide candidate shared secret 510 or CGM 502 does not validate candidate shared secret 510 (e.g., using its stored primary shared secret, or using a shared secret key and secret operations), pairing will fail and trusted communication link 508 will not be established.

By using the process for establishing trusted communication links, mobile computing devices and infusion pumps that are not part of automated insulin therapy system 500 may be restricted from receiving blood glucose level measurement data from CGM 502.

In one or more embodiments, mobile computer device 504 and insulin infusion pump 506 are configured for pairing in accordance with the embodiments for establishing a trusted communication link described in this disclosure. In one embodiment, a shared secret is locally stored at insulin infusion pump 506, and upon request, mobile computing device 504 is configured to provide a candidate shared secret 514 in order to pair with insulin infusion pump 506 and start receiving insulin dosing event information from insulin infusion pump 506. If mobile computing device 504 fails to provide candidate shared secret 514 or if insulin infusion pump 506 does not validate candidate shared secret 514 against its stored primary shared secret, pairing will fail and trusted communication link 512 will not be established. By using the process for establishing trusted communication links, mobile computing devices that are not part of automated insulin therapy system 500 may be restricted from receiving insulin dosing event information from insulin infusion pump 506 and sending insulin dosing instructions to insulin infusion pump 506.

Figure 13A:
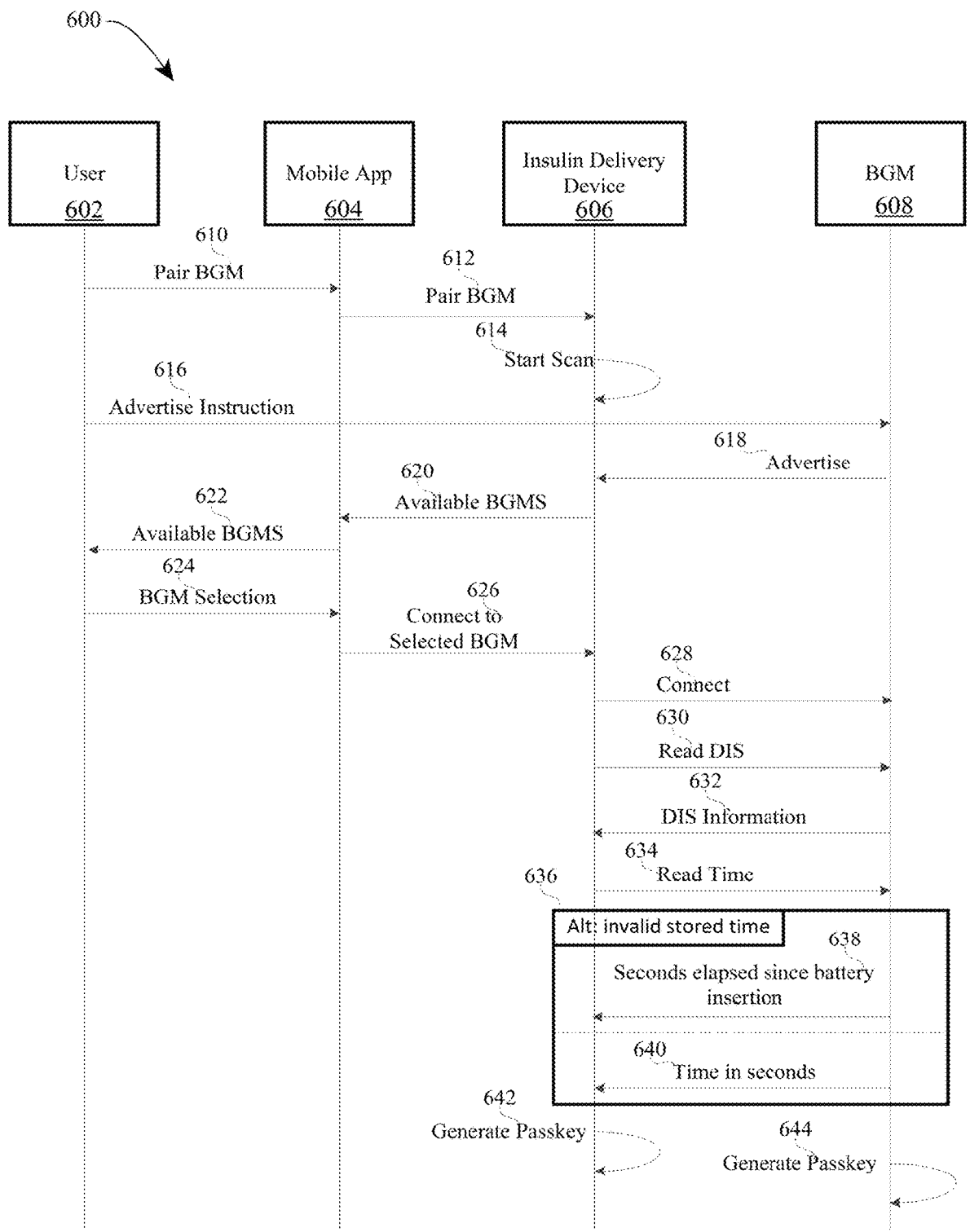
FIGS. 13A and 13B show a sequence of operations that are part of a pairing process between a BGM and an insulin delivery device, in accordance with one or more embodiments of the disclosure.
Figure 13B:
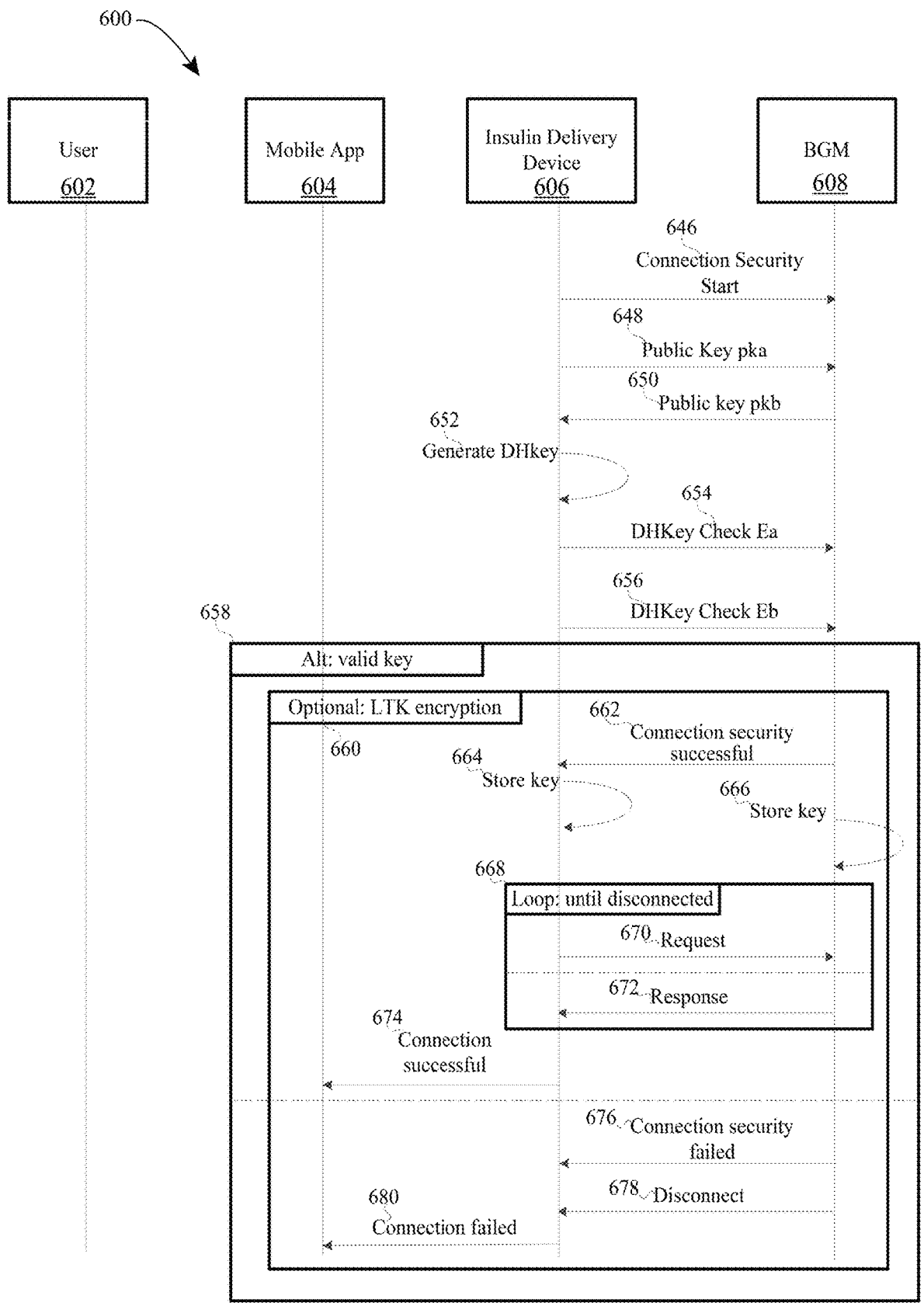

FIGS. 13A and 13B show a sequence of operations that are part of a pairing process 600 performed by a BGM 608, mobile application 604, and insulin delivery device 606 (e.g., an insulin injection pen, medication delivery accessory such as a pen cap, an insulin infusion pump, etc.) that together form, at least in part, an insulin therapy system, in accordance with one or more embodiments of the disclosure. One or more operations of pairing process 600 may be performed by a user 602 of the insulin therapy system. In one or more embodiments, operations indicated as performed by a user may be performed by a user action to activate GUI elements, actuate buttons, speaking voice commands, physically performing pre-defined motions (e.g., waiving a device near another device), etc. Performing the user action(s) initiates some recognition of the action and therefore the operation(s) at a device that is acted on. However, this is not intended to limit this disclosure to requiring a specific user action(s). For example, one or more embodiments may include a recognition of a user action or what is assumed to be a user action, but not the user action itself.

In operation 610, user 602 provides BGM pairing instruction to mobile application 604. In operation 612, mobile application 604 provides a BGM pairing instruction to insulin delivery device 606 responsive to the BGM pairing instruction received in operation 610. Pairing operations between insulin delivery device 606 and BGM 608 are initiated by insulin delivery device 606 and BGM 608 "discovering" each other. In operation 614, insulin delivery device 606 enters a scanning mode responsive to receiving the BGM pairing instruction in operation 612, and scans for advertising messages. In operation 616, user 602 provides an advertise instruction to BGM 608, for example, but actuating a button for some pre-defined period of time. In operation 618, BGM enters and advertising mode and sends advertisement messages that may be received by nearby devices. In operation 620, insulin delivery device 606 sends to mobile application 604 an available BGM list comprising one or more identifiers for available BGM devices (e.g., unique BGM devices for which advertisement messages have been received in the most recent scan mode period), including an identifier for BGM 608. In operation 622, mobile application 604 presents the available BGM list at a display for user 602. In operation 624, user 602 provides a BGM selection to mobile application 604, the BGM selection uniquely identifying one of the BGM devices listed in the BGM list. In operation 626, responsive to the selection, mobile application 604 provides a connection instruction to insulin delivery device 606 that, at least in part, identifies the selected BGM device—here, BGM 608.

In operation 628, insulin delivery device 606 provides a connection request to BGM 608 responsive to receiving the connection instruction in operation 626. In operation 630, insulin delivery device 606 provides a read device information service (DIS) request (or some other request for identifying information, without limitation) to BGM 608. In operation 632, BGM 608 provides DIS information (or other identifying information, without limitation) to insulin delivery device 606 responsive to the read DIS request in operation 630.

In operation 634, insulin delivery device 606 provides a read time request to BGM 608. In one embodiment, BGM 608 provides stored time information (e.g., in seconds) to insulin delivery device 606 in operation 640, responsive to the read time request in operation 634. In another embodiment, BGM 608 may determine in operation 636 whether the stored time is usable or unusable (e.g., because it is incorrect). Responsive to a determination that the stored time is usable, BGM 608 may provide the time in seconds in operation 640. Responsive to a determination that the stored time is not usable, BGM 608 may provide the seconds elapsed since last battery insertion in operation 638.

In operation 642, insulin delivery device 606 generates a passkey responsive to the time information received in operations 640 (or in operation 638) and the DIS information received in operation 632. At about the same time as operation 642, in operation 644 BGM 608 generates a passkey responsive to the time information sent in operation 640 and the DIS information sent in operation 632.

In operation 646, insulin delivery device 606 provides a connection security start request to BGM 608 to attempt to establish a trusted communication link between insulin delivery device 606 and BGM 608. In operation 648, insulin delivery device 606 provides an authentication request that includes a public key "pka" to BGM 608. In operation 650, BGM 608 provides a public key "pkb" to BGM 608 responsive to receiving the authentication request in operation 648. Up receipt of "pkb," insulin delivery device 606 and BGM 608 may send and receive messages using public key encryption.

In operation 652, insulin delivery device 606 generates DHkey, which is a candidate shared secret, in accordance with tone or more processes for generating candidate shared secrets of this disclosure. In operations 654 and 656, insulin delivery device 606 provides a verification request to BGM 608 that includes DHKey encrypted using the public encryption keys "pka" and "pkb."

In operation 658, BGM 608 determines whether DHkey is a valid key or an invalid key in accordance with one or more processes for validating candidate shared secrets of this disclosure. Responsive to determining that DHkey is an invalid key, in operation 676 BGM 608 provides a connection security failure response to insulin delivery device 606, and in operation 678 BGM 608 sends a disconnect message to insulin delivery device 606 to end the untrusted communication link, and terminates the link locally. In operation 680, insulin delivery device 606 sends a connection failure message to mobile application 604, which, in one or more embodiments, presents a failure message to user 602.

Responsive to determining that DHkey is a valid key, in operation 662, BGM 608 sends a connection successful message to insulin delivery device 606 and stores the DHkey in operation 666. In operation 664, insulin delivery device 606 stores the DHkey responsive to receiving the connection successful message provided in operation 662. In operation 674, insulin delivery device 606 provides a connection successful message to mobile application 604.

In one or more embodiments, insulin delivery device 606 and BGM 608 may be configured to continuously perform a truncated authentication process 668 while the trusted communication link is active. In operation 670, insulin delivery device 606 may provide a request to continue the trusted communication link to BGM 608. The request may include DHkey or a new key that is the result of modifying DHkey according to some pre-agreed operations. In operation 672, BGM 608 may provide a response message indicating that the truncated authentication was successful, for example, responsive to validating the DHkey or new key received from insulin delivery device 606 in operation 670.

While one-way sharing of candidate shared secrets has been generally described in this disclosure, one of ordinary skill in the art would understand that two-way sharing of candidate shared secrets is within the scope of the disclosure. When two therapy devices attempt to pair, each therapy device may require the other therapy device to provide a shared secret in order to establish a trusted communication link. In one or more embodiments that implement two-way sharing, each therapy related device may include means for requesting, generating, and/or retrieving a candidate shared secret to provide to the other therapy related device. Similarly, each therapy related device may include means for validating a received candidate shared secret.

One or more of shared secrets, shared secret parameters, secret keys, and secrete operations, may be stored on therapy devices at manufacture or during an initial setup. For example, before an analyte monitoring unit is provided to a patient, the serial number may be used to generate a shared secret that is stored at the monitoring unit and provided either to the patient's specially configured mobile computing device or a remote therapy management system. Alternatively or in addition, the operations used to generate the shared secret may be provided to the patient's specially configured mobile computing device or the remote therapy management system along with the parameters used to generate the shared secret.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It should be understood by a person of ordinary skill in the art that the signal may represent a bus of signals, wherein the bus may have a variety of bit widths and the disclosure may be implemented on any number of data signals including a single data signal.

It should be understood that any reference to an element herein using a designation such as "first," "second," and so forth does not limit the quantity or order of those elements, unless such limitation is explicitly stated. Rather, these designations are used herein as a convenient method of distinguishing between two or more elements or instances of an element. Thus, a reference to first and second elements does not mean that only two elements can be employed or that the first element must precede the second element in some manner. Also, unless stated otherwise a set of elements may comprise one or more elements. Likewise, sometimes elements referred to in the singular form may also include one or more instances of the element.

Many of the functional descriptions in this specification may be illustrated, described or labeled as modules, threads, steps, or other segregations of programming code, including firmware, in order to more particularly emphasize their implementation independence. Modules may be at least partially implemented in hardware, in one form or another. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented using software or firmware, stored on a physical storage device (e.g., a computer readable storage medium), in memory, or a combination thereof for execution by various types of processors.

An identified module of executable code may, for instance, comprise one or more physical or logical blocks of computer instructions, which may, for instance, be organized as a thread, object, procedure, or function. Nevertheless, the executable of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several storage or memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the software portions are stored on one or more physical devices, which are referred to herein as computer readable media.

In some embodiments, the software portions are stored in a non-transitory state such that the software portions, or representations thereof, persist in the same physical location for a period of time. Additionally, in some embodiments, the software portions are stored on one or more non-transitory storage devices, which include hardware elements capable of storing non-transitory states and/or signals representative of the software portions, even though other portions of the non-transitory storage devices may be capable of altering and/or transmitting the signals. Examples of non-transitory storage devices are flash memory and random-access-memory (RAM). Another example of a non-transitory storage device includes a read-only memory (ROM) which can store signals and/or states representative of the software portions for a period of time. However, the ability to store the signals and/or states is not diminished by further functionality of transmitting signals that are the same as or representative of the stored signals and/or states. For example, a processor may access the ROM to obtain signals that are representative of the stored signals and/or states in order to execute the corresponding software instructions.

Some embodiments of the disclosure include or are described as implementing a server. A server is a computer program that provides functionality or services to other programs, commonly called clients. While a server is a computer program or process (i.e., executing program), the term may also be used to refer to a computer running one or more server programs, and so, unless otherwise indicated, the use of the term server in this description is intended to cover both situations. Further, the term computer is intended to cover a single machine, several machines (e.g., a server farm), as well as virtual clusters of computers that emulate one or more hardware elements including without limitation central processing units, graphics processing units, local and system memory, memory storage (e.g., hard disks and solid state drives), operating systems, and networking equipment.

Any characterization in this disclosure of something as 'typical,' 'conventional,' or 'known' does not necessarily mean that it is disclosed in the prior art or that the discussed aspects are appreciated in the prior art. Nor does it necessarily mean that, in the relevant field, it is widely known, well-understood, or routinely used.

While the present disclosure has been described herein with respect to certain illustrated embodiments, those of ordinary skill in the art will recognize and appreciate that the present invention is not so limited. Rather, many additions, deletions, and modifications to the illustrated and described embodiments may be made without departing from the scope of the invention as hereinafter claimed along with their legal equivalents. In addition, features from one embodiment may be combined with features of another embodiment while still being encompassed within the scope of the invention as contemplated by the inventor.

What is claimed is:

1. A medication delivery electronics, comprising:
   a first communication interface configured to communicate with a remote therapy management system;
   a second communication interface configured to communicate with a first therapy device via a first communication link and with a therapy management application via a first trusted communication link, wherein the first trusted communication link is established by the second communication interface in response to verifying a candidate shared secret;
   a connection manager configured to:
      request a first value from the remote therapy management system via the first communication interface, the first value comprising a first variable component and a first pre-defined component, wherein the first pre-defined component is a unique identifier associated with the first therapy device;
      receive the first value from the remote therapy management system responsive to a determination by the remote therapy management system that establishing a trusted communication link would not violate one or more therapy related policies defined by the remote therapy management system;
      hash the first value to generate a first hash key;
      generate a candidate shared secret key responsive to the generated first hash key; and
      provide, via the second communication interface, the candidate shared secret key to the first first therapy device over the first communication link, wherein the candidate shared secret is verified based on the candidate shared secret key, and
   the therapy management application configured to receive, via the second communication interface, first therapy related information from the first therapy device over the first trusted communication link.

2. The medication delivery electronics of claim 1, wherein the pre-defined component comprises a unique identifier component.

3. The medication delivery electronics of claim 1, wherein the unique identifier is a serial number associated with the first therapy device or a public identifier associated with the first therapy device.

4. The medication delivery electronics of claim 1, wherein the first communication link is an intermediate communication link and the second communication interface is configured to end the intermediate communication link responsive to the first trusted communication link being established.

5. The medication delivery electronics of claim 1, wherein the first therapy device is an analyte monitoring device selected from a group consisting essentially of: a blood glucose meter and a continuous glucose monitor, and the therapy related information comprises blood glucose levels and timing information related to the blood glucose levels.

6. The medication delivery electronics of claim 1, wherein: the connection manager is configured to:
   hash a second value to generate a second hash key, the second value comprising a second variable component and a second pre-defined component;
   generate a second candidate shared secret key responsive to the generated second hash key;
   provide, via the second communication interface, the second candidate shared secret key to a second therapy device over a second intermediate communication link established by the second communication interface, and
   the therapy management application configured to send, via the second communication interface, second therapy related information to the second therapy device over a second trusted communication link established by the second communication interface responsive to acceptance of a second candidate shared secret.

7. The medication delivery electronics of claim 6, wherein:
   the first therapy device is a blood glucose meter and the first therapy related information comprises blood glucose levels and timing information related to the blood glucose levels; and
   the second therapy device is an insulin delivery device and the second therapy related information comprises insulin dosing action data.

8. The medication delivery electronics of claim 7, wherein the medication delivery electronics is incorporated into an accessory unit, the accessory unit adapted to releasably and re-attachably couple to the insulin delivery device.

9. The medication delivery electronics of claim 8, wherein the insulin delivery device is selected from a group consisting essentially of an insulin pen, an insulin inhaler, and a syringe.

10. The medication delivery electronics of claim 1, wherein the first therapy device is a continuous glucose monitor and the first therapy related information comprises glucose values and timing information related to the glucose values.

11. The medication delivery electronics of claim 10, further comprising a digital controller configured to automatically control insulin delivery by an infusion pump responsive to the first therapy related information.

12. The medication delivery electronics of claim 11, wherein the connection manager is configured to:
 hash a second value to generate a second hash key, the second value comprising a second variable component and a second pre-defined component;
 generate a second candidate shared secret key responsive to the generated second hash key;
 provide, via the second communication interface, the second candidate shared secret key to a therapy recommendation application executing at a mobile device over a second intermediate communication link established by the second communication interface, and
 the therapy management application configured to send, via the second communication interface, second therapy related information to the therapy recommendation application over a second trusted communication link established by the second communication interface responsive to acceptance of a second candidate shared secret.

13. The medication delivery electronics of claim 12, wherein the therapy recommendation application is configured to determine therapy recommendations based on first therapy related information and user provided therapy information.

14. The medication delivery electronics of claim 13, wherein the user provided therapy information comprises one or more of physiological information, therapy-relevant event information, and projected therapy-relevant information.

\* \* \* \* \*